US008370068B1

(12) United States Patent
Fernandez

(10) Patent No.: US 8,370,068 B1
(45) Date of Patent: *Feb. 5, 2013

(54) INTEGRATED BIOSENSOR AND SIMULATION SYSTEM FOR DIAGNOSIS THERAPY

(76) Inventor: Dennis S. Fernandez, Atherton, CA (US)

( * ) Notice: Subject to any disclaimer, the term of this patent is extended or adjusted under 35 U.S.C. 154(b) by 842 days.

This patent is subject to a terminal disclaimer.

(21) Appl. No.: 12/114,664

(22) Filed: May 29, 2008

Related U.S. Application Data

(63) Continuation of application No. 10/646,682, filed on Aug. 22, 2003.

(51) Int. Cl.
*G01N 33/48* (2006.01)
*G06G 7/48* (2006.01)
(52) U.S. Cl. ............................................ 702/19; 703/11
(58) Field of Classification Search ........................ None
See application file for complete search history.

(56) References Cited

U.S. PATENT DOCUMENTS

| | | |
|---|---|---|
| 5,076,271 A | 12/1991 | Lekholm et al. |
| 5,328,847 A | 7/1994 | Case et al. |
| 5,390,238 A | 2/1995 | Kirk et al. |
| 5,441,047 A | 8/1995 | David et al. |
| 5,594,638 A | 1/1997 | Iliff |
| 5,632,041 A | 5/1997 | Peterson et al. |
| 5,672,686 A | 9/1997 | Chittenden |
| 5,706,498 A | 1/1998 | Fujimiya et al. |
| 5,736,342 A | 4/1998 | Van Wie et al. |
| 5,764,923 A | 6/1998 | Tallman et al. |
| 5,784,635 A | 7/1998 | McCallum |
| 5,810,735 A | 9/1998 | Halperin et al. |
| 5,822,544 A | 10/1998 | Chaco et al. |
| 5,837,832 A | 11/1998 | Chee et al. |
| 5,856,174 A | 1/1999 | Lipshutz et al. |
| 5,874,219 A | 2/1999 | Rava et al. |
| 5,876,926 A | 3/1999 | Beecham |
| 5,968,755 A | 10/1999 | Roederer et al. |
| 5,994,075 A | 11/1999 | Goodfellow |
| 6,042,548 A | 3/2000 | Giuffre |
| 6,064,754 A | 5/2000 | Parekh et al. |
| 6,112,116 A | 8/2000 | Fischell et al. |
| 6,122,536 A | 9/2000 | Sun et al. |
| 6,168,948 B1 | 1/2001 | Anderson et al. |
| 6,178,349 B1 | 1/2001 | Kieval |
| 6,183,963 B1 | 2/2001 | Sinnett et al. |
| 6,197,595 B1 | 3/2001 | Anderson et al. |
| 6,207,392 B1 | 3/2001 | Weiss et al. |
| 6,221,585 B1 | 4/2001 | Iris et al. |
| 6,246,975 B1 | 6/2001 | Rivonelli et al. |
| 6,272,379 B1 | 8/2001 | Fischell et al. |
| 6,278,794 B1 | 8/2001 | Parekh et al. |
| 6,285,897 B1 | 9/2001 | Kilcoyne et al. |
| 6,291,182 B1 | 9/2001 | Schork et al. |
| 6,300,141 B1 | 10/2001 | Segal et al. |
| 6,315,720 B1 | 11/2001 | Williams et al. |
| 6,317,719 B1 | 11/2001 | Schrier et al. |
| 6,358,202 B1 | 3/2002 | Arent |
| 6,379,971 B1 | 4/2002 | Schneider et al. |
| 6,381,025 B1 | 4/2002 | Bornhop et al. |
| 6,389,428 B1 | 5/2002 | Rigault et al. |
| 6,395,480 B1 | 5/2002 | Hefti |
| 6,399,365 B2 | 6/2002 | Besemer et al. |
| 6,402,689 B1 | 6/2002 | Scarantino et al. |
| 6,409,674 B1 | 6/2002 | Brockway et al. |
| 6,423,001 B1 | 7/2002 | Abreu et al. |
| 6,428,951 B1 | 8/2002 | Michnick et al. |
| 6,432,050 B1 | 8/2002 | Porat et al. |
| 6,454,708 B1 | 9/2002 | Ferguson et al. |
| 6,458,086 B1 | 10/2002 | Franco et al. |
| 6,475,750 B1 | 11/2002 | Han et al. |
| 6,486,588 B2 | 11/2002 | Doron et al. |
| 6,490,030 B1 | 12/2002 | Gill et al. |
| 6,514,689 B2 | 2/2003 | Han et al. |
| 6,542,858 B1 | 4/2003 | Grass et al. |
| 6,544,193 B2 | 4/2003 | Abreu et al. |
| 6,546,268 B1 | 4/2003 | Ishikawa et al. |
| 6,546,269 B1 | 4/2003 | Kurnik |
| 6,551,838 B2 | 4/2003 | Santini, Jr. et al. |
| 6,553,244 B2 | 4/2003 | Lesho et al. |
| 6,558,957 B1 | 5/2003 | Roinestad et al. |
| 6,561,978 B1 | 5/2003 | Conn et al. |
| 6,575,912 B1 | 6/2003 | Turcott |
| 6,610,489 B2 | 8/2003 | Wolffe et al. |
| 6,887,714 B2 | 5/2005 | Fritsch et al. |
| 6,970,741 B1 | 11/2005 | Whitehurst et al. |
| 6,994,245 B2 | 2/2006 | Pinchot |
| 7,147,441 B2 | 12/2006 | Fritsch et al. |
| 7,467,928 B2 | 12/2008 | Fakunle et al. |
| 7,542,959 B2 | 6/2009 | Barnhill et al. |
| 7,563,882 B2 | 7/2009 | Zauderer et al. |
| 7,750,125 B2 | 7/2010 | Zauderer et al. |
| 7,932,039 B2 | 4/2011 | Agarwal et al. |

(Continued)

FOREIGN PATENT DOCUMENTS

| | | |
|---|---|---|
| EP | 0867830 A2 | 9/1998 |
| EP | 1318472 | 6/2003 |

(Continued)

OTHER PUBLICATIONS

U.S. Appl. No. 11/644,420, filed Dec. 22, 2006, Fernandez, Dennis S.

(Continued)

*Primary Examiner* — Eric S DeJong
(74) *Attorney, Agent, or Firm* — Fernandez & Associates, LLP

(57) ABSTRACT

BioMEMS/NEMS appliance biologically monitors an individual, using biosensors to detect cellular components. Data is simulated or analyzed using systems-biology software, which provides diagnostic or therapeutic guidance.

2 Claims, 12 Drawing Sheets

U.S. PATENT DOCUMENTS

| | | |
|---|---|---|
| 2001/0023078 A1 | 9/2001 | Bawendi et al. |
| 2001/0034034 A1 | 10/2001 | Bruchez et al. |
| 2002/0019022 A1 | 2/2002 | Dunn et al. |
| 2002/0019347 A1 | 2/2002 | Guegler et al. |
| 2002/0127561 A1 | 9/2002 | Bee et al. |
| 2002/0133495 A1 | 9/2002 | Rienhoff, Jr. |
| 2002/0151816 A1 | 10/2002 | Rich et al. |
| 2002/0197632 A1 | 12/2002 | Moskowitz |
| 2003/0008407 A1 | 1/2003 | Fu |
| 2003/0023388 A1 | 1/2003 | Wagner |
| 2003/0027223 A1 | 2/2003 | Muraca |
| 2003/0033168 A1 | 2/2003 | Califano et al. |
| 2003/0060726 A1 | 3/2003 | Lin et al. |
| 2003/0188326 A1 | 10/2003 | D'Andrea et al. |
| 2004/0006433 A1 | 1/2004 | Robson et al. |
| 2004/0030503 A1 | 2/2004 | Arouh et al. |
| 2004/0088116 A1 | 5/2004 | Khalil et al. |
| 2005/0101841 A9 | 5/2005 | Kaylor et al. |
| 2007/0037164 A1 | 2/2007 | Stanton |
| 2008/0299094 A1 | 12/2008 | Oren |

FOREIGN PATENT DOCUMENTS

| | | |
|---|---|---|
| EP | 1-246-114 A3 | 7/2004 |
| EP | 1507216 | 2/2005 |
| GB | 2325760 A | 12/1998 |
| GB | 2405203 B | 8/2004 |
| GB | 2441078 A | 11/2007 |
| WO | WO-94/00818 | 1/1994 |
| WO | 9622574 | 7/1996 |
| WO | WO-97/09678 A | 3/1997 |
| WO | WO 97/27560 A1 | 7/1998 |
| WO | WO 98/35609 A1 | 8/1998 |
| WO | WO 00/28893 A1 | 5/2000 |
| WO | WO-00/43552 A3 | 7/2000 |
| WO | 0169244 | 9/2001 |
| WO | WO-01/78652 A | 10/2001 |
| WO | WO-02/06266 A | 1/2002 |
| WO | WO-02/06566 A1 | 1/2002 |
| WO | WO-02/09119 A1 | 1/2002 |
| WO | WO-02/24862 A3 | 3/2002 |
| WO | WO 02/25528 A1 | 3/2002 |
| WO | 02065119 | 8/2002 |
| WO | WO-02/091119 | 11/2002 |
| WO | WO-02/91119 A | 11/2002 |
| WO | 02103608 | 12/2002 |
| WO | WO-03/005628 A | 1/2003 |
| WO | WO-03/017177 A | 2/2003 |
| WO | WO-03/043684 A | 5/2003 |
| WO | 03077062 | 9/2003 |
| WO | 2004047020 | 6/2004 |

OTHER PUBLICATIONS

Sandra J. Rosenthal, "Bar-coding biomolecules with fluorescent nanocrystals", Nature Biotechnology, 2001, pp. 621-622, vol. 19, Issue 7, Nature Publishing Group, NYC, US.

Easterling, et al., "Comparative Analysis of Software for Physiologically Based Pharmacokinetic Modeling: Simulation, Optimization, and Sensitivity Analysis", in Toxicology Methods, Jul. 2000, vol. 10, Issue 3, pp. 203-220.

GenCore version 6.3, USPTO Examiner's search, Run on Sep. 1, 2010 on "OM nucleic—nucleic search, using sw model".

Warren, et al., "VCSEL Applications in Sensors and Microsystems", SPIE (1998), vol. 3286, pp. 42-51.

"Delivering Pharmacogenomics."DxS Limited. 2003 (online). Manchester, United Kingdom. Retrieved from the Internet: <URL: http://www.dxsgenotyping.com>.

"Clinical Services."DxS Limited. 2003 (online). Manchester, United Kingdom. Retrieved from the Internet: <URL: http://www.dxsgenotyping.com>.

Weber, Wendell, "The Legacy of Pharmacogenetics and potential Applications", (2001), pp. 1-18, vol. 479, Elsevier.

Schoeneberg, T. et al., "Mutant G-protein-coupled receptors as a cause of human diseases", Pharmacology & Therapeutics, 2004, pp. 173-206, vol. 104, Elsevier, Amsterdam/Holland.

Oetting, W. S. et al., "Linkage Analysis with Multiplexed Short Tandem Repeat Polymorphisms Using Infrared Fluorescence and M13 Tailed Primers", Genomics, 1995, vol. 30, pp. 450-458, Elsevier, Amsterdam/The Netherlands.

Wood, A., "Racial Differences in the Response to Drugs—Pointers to Genetic Differences", New England Journal of Medicine, May 3, 2001, pp. 1393-1396, vol. 344, No. 18, Massachusetts Medical Society, Waltham, Mass/US.

Han M., et al. "Quantum-dot-tagged microbeads for multiplexed optical coding of biomolecules", Nature Biotechnology, 2001, pp. 631-635, Jul. 2001, vol. 19, <URL: http://www.genxy.com/Business/bus_pharmaco.html>.

U.S. Appl. No. 10/277,213, filed Oct. 18, 2002, Fernandez.
U.S. Appl. No. 11/140,438, filed May 26, 2005, Fernandez.
U.S. Appl. No. 11/585,519, filed Oct. 23, 2006, Fernandez.
U.S. Appl. No. 11/703,508, filed Feb. 6, 2007, Fernandez.
U.S. Appl. No. 11/703,331, filed Feb. 6, 2007, Fernandez.
U.S. Appl. No. 12/115,508, filed May 5, 2008, Fernandez.
U.S. Appl. No. 12/239,563, filed Sep. 26, 2008, Fernandez.
U.S. Appl. No. 12/351,358, filed Jan. 9, 2009, Fernandez.
U.S. Appl. No. 12/351,552, filed Jan. 9, 2009, Fernandez.
U.S. Appl. No. 11/285,920, filed Nov. 23, 2005, Fernandez.
U.S. Appl. No. 11/385,054, filed Mar. 20, 2006, Fernandez.
U.S. Appl. No. 11/646,420, filed Dec. 22, 2006, Fernandez.
U.S. Appl. No. 11/949,256, filed Dec. 3, 2007, Fernandez.
U.S. Appl. No. 12/239,026, filed Sep. 26, 2008, Fernandez.
U.S. Appl. No. 12/423,591, filed Apr. 14, 2009, Fernandez.
U.S. Appl. No. 12/423,230, filed Apr. 14, 2009, Fernandez.
U.S. Appl. No. 12/423,275, filed Apr. 14, 2009, Fernandez.
U.S. Appl. No. 12/423,340, filed Apr. 14, 2009, Fernandez.
U.S. Appl. No. 12/423,420, filed Apr. 14, 2009, Fernandez.
U.S. Appl. No. 12/423,548, filed Apr. 14, 2009, Fernandez.
U.S. Appl. No. 12/541,146, filed Aug. 13, 2009, Fernandez.

Lennard et al. "Congenital Thiopurine Methyltransferase Deficiency and 6-Mecaptopurine Toxicity During Treatment for Acute Lymphoblastic Leukemia," Arch. Dis. Child., vol. 69 (1993), pp. 577-579.

Saffo, Paul. "Sensors: The Next Wave of Infotech Innovation." Institute for the Future, 1997 Ten Year Forecast (1997), pp. 115-122.

Mechkour. M. et al. "Prime—GC, A Medical Information Retrieval Prototype on the Web", Proc. 7th International Workshop on Research Issues in Data Engineering, Apr. 7-8, 1997.

Grigsby et al., "Telemedicine: Where it is and where it's going." Annals of Internal Medicine, vol. 129, No. 2 (Jul. 15, 1998), p. 123-126.

Institute for the Future, "Twenty-First Century Health Care Consumers", Health Care Horizons Program Report. Executive Summary (1998) p. 1-5.

Ganguly, Pronab et al., "Telemedicine over enterprise—wide networks: a case study", IEEE Global Telecommunications Conference (GLOBECOM98), Sydney, Nov. 1998, p. 1297-1302.

Pavlopoulos, S. et al. "Design and development of a web-based hospital information system." Proceedings of the 20th Annual Int'l Conference of the IEEE, Nov. 1998. p. 1188-1191.

Long, R. et al. "Understanding Individual Variations in Drug Responses: from Phenotype to Genotype." National Institute of General Medical Sciences [online], Jun. 9-10, 1998. [Retrieved on Jun. 27, 2002]. Retrieved from the internet: <URL: http://nigms.nih.gov/news/reports/pharmacogenetics.html>.

"Pharmacogenetics in Patient Care." AACC [online] Nov. 6, 1998. [Retrieved on Jul. 20, 2002] Retrieved from the Internet: <URL: http://www.aacc.org/pharmacogenetics/>.

Ferratt, Thomas et al.,Surmounting Health Information Network Barriers;the greater Dayton area experience.Health Care Management. Winter 1998 p. 70-76(Aspen Publishers, Boston).

"What is Pharmacogenomics?"IMPACT[online].Jun. 1999 [Retrieved on Jun. 27, 2002] Retrieved from the Internet:<URL:http://uscf.edu/foundation/impact/archives/1999/17-pharmacog.html.

Atalay, Besin et al. "HIVPCES: A www-based HIV Patient Care Expert System, IEEE." (Jun. 18, 1999) p. 214-219.

Baker, Dixie et al."A Design for Secure Communication of Personal Health Information Via the Internet."Medical Informatics. Mar. 20, 1998 vol. 54 p. 97-104 (Elsevier, Amsterdam).

Malamateniou, F. et al.,"A search engine for virtual patient record." Medical Informatics. Feb. 8, 1999 vol. 55. p. 103-115. (Elsevier, Amsterdam).

Aizawa, Masuo et al. "Protein Engineering for Biosensors." Protein Engineering in Industrial Biotechnology, p. 246-265 (Harwood Academic Publishers, 2000 Italy.).

Mendible, Juan. C., "Pharmacogenomics: Medicines Tailored Just for You," [online] Jan. 3, 2000. Retrieved from the Internet: <URL: http://www.suite101.com/print article>.

Jing Kong, Nathan R. Franklin, Chongwu Zhou, Michael G. Chapline, Shu Peng, Kyeongjue Cho, Hongjer Dui, "Nanotube Molecular Wires as Chemical Sensors" Science Mag. [online] Jan. 28, 2000 [Retrieved on May 27, 2002] Retrieved from the Internet: <URL: http://sciencemag.org>.

Davis, Allison. "NIH effort to Understand How Genes Affect People's responses to Medicines. "NIGMS [online] Apr. 4, 2000. [Retrieved on Jun. 27, 2002] Retrieved from the Internet: <URL: http://www.nigms.nih.gov/news/releases/pharmacognetics.html>.

Thompson, Cheryl. "NIH starts pharmacogenetics network." American Society of Health Systems Pharmacists [online] Apr. 27, 2000. [Retrieved on Jul. 20, 2002] Retrieved from the Internet: <URL: http://www.org.nigms.nih.gov/news/releases/pharmacognetics.html>.

Lathrop, J. et al., "Health Care New Electronic Marketplace." Strategy Business. vol. 19 (Apr.-Jun. 1999) p. 34-43.

Richards, Joy "Nursing in a Digital Age," Nursing Economics vol. 19, No. 1 (Jan.-Feb. 2001) p. 6-34.

Hensley, Scott et al., "Next Milestone in Human Genetics," The Wall Street Journal, May 26, 2000. p. B1.

Gulcher, Jeffry et al., "The Icelandic Healthcare Database and Informed Consent," The New England Journal of Medicine, vol. 342, No. 24 (Jun. 2000) p. 1-5.

Idekker, Trey et al., "A New Approach to Decoding Life: Systems Biology," Annul. Rev. Genomics Hum. Gen. vol. 2 (2001) p. 343-372.

The Power of Pharmacogenetics: TPMT, DNA Sciences Laboratories. [online] 2002. Retrieved from the Internet: <URL://www.DNASciences.com>.

Hollon, Tom. "The Making of the Pharmacogenomic Prescription." Geneletter [online] Jan. 2, 2001. [retrieved on Jun. 27, 2002]. Retrieved from the Internet<URL: www.geneletter.com/01-02-01/features>.

Khoury, Muin et al., "Will Genetics Revolutionize Medicine?" Geneletter [online], Jan. 2, 2001. [retrieved on Jun. 27, 2002] Retrieved from the Internet: <URL: www.geneletter.com/01-02-01/features>.

Khoury, M. et al., "Pharmacogenomics & Public Health: The Promise of Targeted Disease Prevention." CDC [online], Jan. 15, 2001 Retrieved from the Internet: <URL: http://www.cdc.gov/genomics/info/factshts/html>.

Walsh, Barbara."Genotyping for prescriptions underutilized." Geneletter [online], Jan. 2, 2001. [retr. on Jun. 27, 2002] Retrieved from the Internet: <http://www.geneletter.com>.

Lipp, Elizabeth. Pharmacogenetics Research & Methodologies. Genetic Engineering News. Feb. 15, 2001 vol. 21 (4) p. 21-26.

Davis, Alison, et al. "Pharmacogenomics Research Network & Knowledge Base." Pharmacogenomics. vol. 2 , No. 3 (Apr. 25, 2001) p. 285-289.

"Pharmacogenomics: Finding the Competitive Edge in Genetic Variation," Cambridge Health Institute [online] 2001 [retrieved on Jun. 27, 2002] Retrieved from the Internet: <URL: http://www.chireports/com/content/reports/toc/printpage/asp?R/pharmacogenomics01.toc.AS>.

"Pharmaco-Genetics: Finding the Right Medicine for each Patient." DNA Sciences. [online], May 4, 2001. [retrieved on Jul. 20, 2002] <URL: http://www.ppgx/com>.

"Pharmacogenomics." Human Genome Project Information.[online] May 29, 2001 [retrieved on Aug. 27, 2002] <URL: http://www.ornl.gov/hgmis/medicine/pharma/html.

"The Good of Small Things," Science and Technology [online] Dec. 20, 2001. [retrieved on Jan. 11, 2002] Retrieved from the Internet: <URL: http://www.economist.com>.

"Veri Chip" Datasheet from applied digital solutions corp. [online] Dec. 19, 2001. [retrieved on Dec. 19, 2001] URL:http://www/adsx/com/verichip/verichip/html.

Johnson, Colin, "Smart Sensors Extend Web Scale,"EE Times [online], Apr. 26, 2001. [retrieved on Dec. 19, 2001] Retrieved from the Internet: <URL: http://www.eet.com>.

Sadee, Wolfgang et al. "Genetic Variations in Human G-Protein-coupled receptors: Implications for Drug Therapy." AAPS Pharmaceutical [online], Jul. 26, 2001. [retrieved on Jun. 27, 2002] Retrieved from the Internet:<URL: http://www.pharamsci/org/scientifcjournals/pharmsci/journa1/01-22.html>.

Aldrige, Susan "Customizing Drugs to Individual Genetic Profiles." Genetic Engineering News 2001. vol. 21(14) p. 30.

"Genomics and Its Impact on Medicine and Society." U.S. Department of Energy Human Genome Program [online], Oct. 2001. <www.ornl.gov/hgmis/publicat/primer/intro.html>.

"Categories of Pharmacogenetic Knowledge." PharmGKB [online], 2002 [retrieved on Jun. 27, 2002]. Retrieved from the Internet: <URL:http://www.servesessionid-24A5Etomcat?id=home.welcom>.

Loud, Jennifer et al. Applications of Advances in Molecular Biology and Genomics to Clinical Cancer Care. Cancer Nursing 2002 vol. 25(2) p. 110-122.

"As the Science Succeeds, Patients Benefit." UCSF Center for Pharmacogenomics [online], Mar. 11, 2002[retrieved on Jun. 27, 2002]. Retrieved from the Internet: <URL: http://www.pharmacy.ucsf.edu/cpg/whatis/>.

"Technology Forecasts." Batelle.org [online], 2002 [retrieved on Jul. 27, 2002]. Retrieved from the Internet: <URL: http://www.batelle.org/forecasts/technology2020.stm>.

Scatimel, Bruno. "Biosensors and Proteomics." vLifeScience [online], 2002 [Retrieved on Feb. 3, 2002]. <URL: http://www.vLifeScience/com/au>.

Murray, Charles. "Injectable Chips Opens Door to 'Human Bar Code'." EETIMES [online], Jan. 4, 2002[retrieved on Jan. 4, 2002]. Retrieved from the Internet: <http://www.eet.com>.

"IBM Mayo Clinic to Collaborate on Worldwide Medical Database." SiliconValley.com [online], Mar. 25, 2002 [retrieved on Mar. 25, 2002]. Retrieved from the Internet: <URL:http://www.siliconvalley.com>.

Hamilton, David P. Custom Tailored Medicine. The Wall Street Journal. Mar. 25, 2002 p. B1.

"Huge British gene bank gets $65 Million go-ahead" SiliconValley.com [online], Apr. 29, 2002. [retrieved on Apr. 29, 2002] <URL: http://www.siliconvalley.com>.

Stikeman, Alexander. "Make the Diagnosis." Technology Review [online], May 2002. [retrieved on May 23, 2002] Retrieved from the Internet: <URL: http://www.techonologyreview.com>.

Ohr, Steven. "Sensors seen enabling new-age services." EETimes [online], May 22, 2002. [retrieved on Jun. 5, 2002] Retrieved from the Internet: <URL: http://www.eet.com>.

Stikeman, Alexander. "The State of Biomedicine" Technology Review [online], Jun. 2002. [retrieved on Jun. 5, 2002] Retrieved from the Internet: <URL:http://technologyreview.com/articles/stateof>.

"The Ethics of Patenting DNA." The Nuffield Council on Bioethics. Jul. 2002. The Nuffield Foundation (London, England).

"Technology shapes tomorrow's digital hospital." EETimes [online], Jul. 5, 2002 [retrieved on Jul. 5, 2002]. Retrieved from the Internet: <URL: http://www.eet.com>.

Landro, Laura. "Hospitals' Technology Gap Widens." The Wall Street Journal. (Jul. 16, 2002) p. D3.

Rostler, Suzanne. "Study finds drug errors common in U.S. Hospitals." Reuters [online], Sep. 9, 2002 [retrieved on Sep. 9, 2002] Retrieved from the Internet: www.reuters.com>.

Johnson, Colin: "Synthesis of Nanoparticles Coming into Focus." EETimes [online], Jul. 16, 2002 [retrieved on Jul. 17, 2002] Retrieved from the Internet:< URL: http://www.eet.com>.

Philipkoski, Kristen. "BiochipLDiagnosis in a Pinch." Wired News [online], Jul. 18, 2002 [retrieved on Jul. 18, 2002]. Retrieved from the Internet:< URL: http://www.wired.com>.

"Wyeth Updates Product Labels for its Postmenopausal Hormone Therapies." Wyeth Corp. [online], Sep. 4, 2002 [retrieved on Sep. 6, 2002]. Retrieved from the Internet: <URL: http://www.wyeth.com/news/press>.

Pearson, Helen. "At Home DNA Tests Are here." The Wall Street Journal. (Jun. 25, 2002) p. D6.

Johnson, Colin. "Silicon Nanoparticles Eyed for Chemical Detection." EETimes [online], Sep. 9, 2002 [retrieved on Sep. 9, 2002]. <URL: http://www.eetc.com>.

Veloso,Mario et al. "From Hospital Information System Components to the Medical Record & Clinical Guidelines & Protocols." Medical informatics Europe '97 (1997), p. 300 (IOS, Amsterdam).

"Emerging Infections and Potential Bioterrorist Agents."UAB [online], Oct. 15, 2001 [retrieved on Jan. 7, 2002]. Retrieved from the Internet: <URL: http://www.bioterrorism.uab.edu/emerging%20infection>.

Miller, Krista et al. "I3C Tech Architecture." O'Reilly Bioinformatics Technology Confererence [online], Jan. 31, 2002 [retrieved 2002] <URL: http://www.I3C.org>.

Draetta, Giulio and Boisclair, Michael. "Molecular Bioscreening in Oncology" Protein Engineering in Industrial Biotechnology, p. 356-367(Harwood Academic, 2002).

"Cancer Bioinformatics Infrastructure Objects (caBio)" National Cancer Institute Center for Bioinformatics [online], 2002 [retrieved 2002]. Retrieved from the Internet: <URL: http://www.ncicb.nih.gov/core/caBio>.

"Will pharmacogenomics revolutionize clinical trials?" Datamonitor [online], 2002 [retrieved 2002]. Retrieved from the Internet: <URL: http://www.datamonitor.com~3573982C452997011c2oa~/home>.

"Bioinformatics glossary." Genomic Glossaries [online], Aug. 20, 2002 [Retrieved on Aug. 27, 2002] <URL: http://www.genomicgloassaries.com/content/printpage.asp?REF=/bioinf>.

"The new word in designer drugs." Bmj [online], Jun. 27, 1998 [retrieved on Jun. 27, 2002]. Retrieved from the Internet: <URL: http://www.bmj.com/cgi/content/full/316/7149/1930>.

"Commercialization-Putting our discoveries to work." DNA Sciences [online] 2002. [retrieved on Jul. 20, 2002]. Retrieved from the Internet: <URL: http://www.ppgx/com/sciencediscovery.jsp?site=dna&link=commercialization>.

"Phillips Launches Software to Pinpoint Cancer," Reuters [online] Oct. 10, 2002 [retrieved on Oct. 10, 2002] Retrieved from the Internet: <URL: http://www.reuters.com>.

"Biosensors/Transducer technology." Stanford Biodesign [online], 2002. [retrieved on Sep. 12, 2002] Retrieved from the Internet: <http://www.stanford.edu/group/biodesign/technic>.

"Exact Sciences Issued Patent for Novel Method of Detecting Mutation." Exact Sciences [online], Aug. 6, 2002 [retrieved on Sep. 19, 2002]. Retr. from the Internet: <URL: http://www.exactsciences.com/about/press_releases/exact&sciences&issued&parent&for&novel&method>.

"Metabolomics in Biotech: A revolutionary tool to optimize the production of new leads." TNO pharma [online], 2002 [retrieved on Apr. 11, 2002]. Retrieved from the Internet: <URL: http://www.pharm.t>.

"I3C Technical Meeting Agenda." I3C Consortium [online], Oct. 11, 2002 [retrieved on Oct. 14, 2002] Retrieved from the Internet: <URL: http://www.I3C.org/mtg/past.asp>.

"I3C Backgrounder." I3C Consortium [online], Jun. 23, 2001 [retrieved on Oct. 14, 2002]. Retrieved from the Internet: <URL: http://www.I3C.org/html/i3c_backgrounder.html>.

Neumann, Eric et al. "I3C Pathways." I3C Consortium (online) 2002. [retrieved on Oct. 14, 2002] Retrieved from the Internet:<URL: http://www.i3c.com>.

O'Reilly Bioinformatics Technology Conference, I3C Consortium (online) 2002 [retrieved on Oct. 14, 2002] Retrieved from the Internet: <URL: http://www.i3c.org>.

Abate, Tom. "Proofreading the Human Genome." The San Francisco Chronicle. Oct. 7, 2002. p. E1.

Willing, Richard. "DNA Testing Fails to Live up to Potential." USA Today. (Oct. 7, 2002) p. 1A.

"Comparisons of Mutagenesis Kits." Stratagene Corporation. Advertisement 2002.

Lesko, LJ. et al. "Pharmacogenomic-guided drug development: regulatory perspective." The Pharmacogenomics Journal 2002 (2) p. 20-24.

Sannes, Lucy. "High Content Screening: Parallel analysis fuels accelerated discovery and development." CHI Reports, 2002. Cambridge Health Institute, Newton Upper Falls, MA.

Landro, Laura. "Doctors need computerized offices." The Wall Street Journal. Sep. 5, 2002. pp. D4, Dow Jones & Company, New York, NY.

Merriam Webster Online Dictionary "Join" Retrieved from the Internet: <URL:http://www.merriam-webster.com/dictionary/join>.

"Clinical, Diagnostic and Research Services,"DxS Limited. 2003 (online). Manchester, United Kingdom. Retrieved from the Internet: <URL: http://www.dxsgenotyping.com>.

"SNPs-Primed and Ready to Glow: Pharmacogenomic services enabled by Scorpions™"DxS Limited. 2003 (online). Manchester, United Kingdom. Retrieved from the Internet: <URL: http://www.dxsgenotyping.com>.

Krishnan, S. et al., "A Multimedia-based Medical Database Network System for Special Clinical Procedures in Healthcare Delivery", IEEE/EMBS, (Oct. 30-Nov. 2, 1997) Chicago IL.

Little, Stephen, "Strategic options for delivering pharmacogenomic tests to the patient." GOR, (Feb. 25, 2002) vol. 4, No. 1, Manchester, UK.

Jain, KK. "Applications of Biochip and Microarray Systems in Pharmacogenomics." Pharmacogenomics (Aug. 2000) vol. 1 No. 3, p. 289-307.

Vanderlubbe, R.P., "Flexible Electronic Patient record: first results from a dutch hospital," Medical Informatics Europe '97 (1997) p. 246-251 (IOS, Amsterdam).

Genset, "Business Opportunities Pharmacogenomics: The Science of the Drug Response Genes," [retrieved on Jun. 27, 2002] Retrieved from the Internet: <URL: www.genxy.com>.

Tansey, Bernadette,"Power Tools for the Gene Age," San Francisco Chronicle, (Feb. 7, 2005) p. E1-E2.

Winslow, Ron; Mathews, Anna W., "New Genetic Tests Boost Impact of Drugs." Wall Street Journal, Dec. 21, 2005, p. D1.

Sharapov, Ilya, "Computational Applications for Life Sciences on Sun Platforms: Performance Overview," Market Development Engineering, Sun Microsystems, Inc. Nov. 2001.

"SNPs & other Genetic Variations Glossary." Genomic Glossaries [online], Jul. 19, 2002 [retrieved on Aug. 27, 2002] Retr. from the Internet: <URL: http://www.genomicglossaries.com>.

"Medicine and the New Genetics." USDOE Office of Science, Human Genome Project Information website [online], Sep. 19, 2008 [retrieved on Aug. 5, 2009]. Retrieved from the Internet: <URL: http://www.ornl.gov/sci/techresources/Human_Genome/medicine/medicine.shtml>.

Chang, Chen. "BLAST Implementation on BEE2," Electrical Engineering and Computer Science, Univ. of Cal Berkeley, 2004.

Jacobi, Ricardo P., et al., "Reconfigurable Systems for Sequence Alignment and for General Dynamic Programming," Genet. Mol. Res. 4(3):543-552 (Sep. 30, 2005).

Merriam Webster Online Dictionary "Couple" [retrieved on Jul. 17, 2007] Retrieved from the Internet: <URL: http://www.merriam-webster.com/dictionary/couple>.

Ma, Xiao-Jun., et al., "Gene expression profiles of human breast cancer progression." Proceedings of the National Academy of Sciences of the United States of America [online], Nov. 9, 2002 [retrieved on Jul. 1, 2009]. Retrieved from the Internet: <URL: http://www.pnas.org/content/100/10/5974.abstract>.

U.S. Appl. No. 10/646,682, filed Aug. 22, 2003, Fernandez.

Healey, Jennifer and Gould, Grant, "Affective Jewelry and other Affective Accessories". M.I.T. Media Laboratory. Affective Computing Research Project [online], [retrieved on Jan. 18, 2003]. Retrieved from the Internet: <URL: http://www.media.mit.edu/affect/AC_research/projects/affective_jewelry.html>, pp. 1-5.

Borkholer, David A.; Debusschere, Derek B.; Stenger, David; and Kovacs, Gregory T. A.,"Hybrid Blosensors". Stanford University Transducers Lab. Hybrid Blosensors Project [online], [retrieved on Jan. 18, 2003]. Retrieved from the Internet: <URL: http://transducers.stanford.edu/Projects.html>, pp. 1-4.

Tonnesen, Cindy and Withrow, Gary, "Biosensors". The Encyclopedia of Virtual Environments [online], [retrieved on Jul. 28, 2006]. Retrieved from the Internet: <URL: http://www.hiti.washington.edu/soivw/EVE/I.D.1.c.Biosensors.html>, pp. 1-8.

Debusschere, Derek B., and Kovacs, Gregory T. A., "Portable Cell-Based Biosensors". Stanford University Transducers Lab. Portable Cell-Based Biosensors Project [online], [retrieved on Aug. 8, 2003]. Retrieved from the Internet: <URL: http://transducers.stanford.edu/Projects.html>, pp. 1-3.

Ahn, Chong H. and Choi, Jin-Woo., "Plastic-Based Disposable Smart Biochips with Integrated Biosensors for Blood Analysis and Clinical Diagnostics". University of Cincinnati Department of Electrical & Computer Engineering and Computer Science. MicroSystems and BioMEMS Lab. [retrieved on Aug. 8, 2003]. Retrieved from the Internet: <URL: http://www.healthtech.com/2001/mfb/abstracts/ahn.html>, pp. 1-2.

Elias, Paul, "Biotech Inventors Turn to More Exotic Manipulation". Mall&Guardianonilne [online], Jul. 8, 2003 [retrieved on Jul. 23, 2003]. Retrieved from the Internet: <URL: http://www.mg.co.za/articledirect.aspx?articleid=23925&area=%2fbreaking_news%2fbreaking_news_international_news%2f>, pp. 1-3.

Rogers, Jim and Quick, Julie, "USDA Strengthens 2003 Permit Conditions for Field Testing Genetically Engineered Plants". U.S.D.A. Press Release [online]. [Retrieved before or on Aug. 22, 2003]. Retrieved from the Internet: <URL: http://www.aphls.usda.gov/lpa/news/2003/03/gepermits_brs.html>, pp. 1-2.

Savello, Paul, "Food Safety in the Food Manufacturing Industry". USAID Kosovo Cluster & Business Support Project Press Release. Kosovo Business Support Archive Articles [online], article in "Koha Ditore," Dec. 11, 2002. Available on the Internet at: http://usaidkcbs.com/KBS% 20Archive/KBS%20Articles/121102.htm>, pp. 1-3. [retrieved before or on Aug. 22, 2003].

"Laboratory Tests that Detect Cancer". The Cancer Cure Foundation [online], [retrieved before or on Aug. 22, 2003]. Retrieved from the Internet: <URL: http://www.cancure.org/tests_to_detect_cancer.htm>, pp. 1-10.

Tansey, Bernadette, "Cancer Sleuthing; Bay Area Companies among Those Profiling the Disease". SFGate.com [online], Jul. 6, 2003, [retrieved before or on Aug. 22, 2003]. Retrieved from the Internet: <URL: http://www.sfgate.com/cgi-bin/article.cgi?f=/c/a/2003/07/06/BU246056.DTL&hw=Cancer+sleuthing&sn=001&sc=1000>, pp. 1-2.

"New Test May Improve Cancer Detection". Press Release from Reuters.com [online], [retrieved on Jul. 10, 2003]. Retrieved from the Internet: <URL: http://www.reuters.com/newArticle.jhtml?type=healthNews&Story ID=3112050&fromEmail=true>, 1 page; alternatively available from the Internet: <URL: http://www.cancerpage.com/news/article.asp?id=6132>, 1 page.

"Gene Profiling May Help Treat Cancer; Procedure Could Reduce Unnecessary Use of Certain Drugs", Press Release from MSNBC.com [online], [retrieved before or on Aug. 22, 2003]. Retrieved from the Internet: <URL: http://msnbc.msn.com/id/3076856/>, pp. 1-4.

Medoro, Gianni; Manaresi, Nicolo; Tartagni, Marco; and Guerrieri, Roberto, "CMOS-only Sensors and Manipulators for Microorganisms", from IEEE Xplore.org [online], Aug. 6, 2002, [retrieved before or on Aug. 22, 2003]. Retrieved from the Internet: <URL: http://ieeexplore.ieee.org/xpls/absprintf.jsp?arnumber=904344, pp. 1-11.

"RNA Interference". Science & Technology Release by Sima Therapeutics [online], [retrieved on Jul. 10, 2003]. Retrieved from the Internet: <URL: http://www.sirna.com/wt/page/science>, pp. 1-2.

"New Products-Targefect-siRNA Transfection Kit for RNA Interference Studies" Product Description from Targeting Systems, Santee (CA) [online], [retrieved on Jul. 10, 2003], Retrieved from the Internet: <URL: http://www.tergetingsystems.com/siRNA.pdf, pp. 1-8.

Atanasov, Plamen; Yang, S.; Salehi, C.; Ghindilis, Andrei; and Wilkins, Ebtisam, "Short-term Canine Implantation of a Glucose Monitoring-Telemetry Device", Medical Engineering and Physics, vol. 18, No. 8 (1998), pp. 832-640.

"Medical Micromachines: New ATDC Company Developing Implantable Blood Pre and Flow Sensor Based on Micro Electromechanical Systems (MEMS) Technology", Press Release from Advanced Technology Development Center [online], Jan. 28, 2002 [retrieved before or on Aug. 22, 2003]. Retrieved from the Internet: <URL: http://web.archive.org/web/20030210225423/www.atdc.org/news/january282002.html>, pp. 1-3.

Walli, Ron, "Miniature Implantable Sensor Likely Lifesaver for Patients". News Release from Oak Ridge National Laboratory [online], [retrieved before or on Aug. 22, 2003). Retrieved from the Internet: <URL: http://www.oml.gov/Info/press_releases/get_press_release.cfm?ReleaseNumber=mr20021122-00>, pp. 1-2.

"Research Presented At ADA Annual Meeting Demonstrates Accuracy and Feasibility of Artificial Pancreas Components", News Release from Medtronic [online] [retrieved before or on Aug. 22, 2003]. Retrieved from the Internet: <URL: http://wwwp.medtronic.com/Newsroom/NewsReleaseDetails.do?itemid=1096480090589&lang=en_US>, pp. 1-3.

"IntelliSense Drives MEMS Product Design Development and Manufacturing",Sensor Business Project, vol. 9, No. 9 (Jan. 9, 2000), pp. 65-69, Vital Information Publications, Foster City, CA.

Dichter, Marc A., "An Implantable Device to Predict and Prevent Seizures", 2002 (abstract)National Institute of Neurological Disorders and Stroke [online], pp. 54-55. [retrieved on Aug. 8, 2003]. Retrieved from the Internet: <URL: http://www.nibib.nih.gov/nibib/File/News%20and%20Events/Previous%20Symposia%20and%20Workshops/1516Aug2005/ABSTRACTS.pdf>.

Schwiebert, Loren, "Wireless Networking Solutions for Smart Sensor Biomedical Applications",2000 (abstract). National Science Foundation [online], pp. 1-2, [retrieved on Aug. 8, 2003]. Retrieved from the Internet: <URL: http://shamir.eas.asu.edu/%7emcn/bioabstract.html>.

Eversmann, Bjorn; Jenkner, Martin; Paulus, Christian; Hofmann, Franz; Brederlow, Ralf; Holzapfl, Birgit; Fromherz, Peter; Brenner, Marucus; Schreiter, Matthias; Gabl, Reinhard; Plehnert, Kurt; Steinhauser, Michael;Eckstein, Gerald; Schmitt-Landsiedel, Doris; Thewes, Roland, "A 128x128 CMOS Biosensor Array for Extracellular Recording of Neural Activity", IEEE Journal of Solid-State Circuits, vol. 38, Issue 12 (2003), pp. 2308-2317.

"Chip Senses Trace DNA", Technology Research News from An MIT Enterprise Technology Review [online], Jul. 31, 2003. [retrieved on Aug. 4, 2003]. Retrieved from the Internet: <URL: http://www.technologyreview.com/>, 1 page.

Hui Du, Matthew D. Disney, Benjamin L. Miller, and Todd D. Krauss, "Hybridization-Based Unquenching of DNA Hairpins on AU Surfaces, Prototypical 'Molecular Beacon' Biosensors" Jacs, J. Am. Chem. Soc., 125:4012-13(2003).

"The Outcry over 'Terminator' Genes in Food," Business Week on line, pp. 1-3, retrieved Jul. 14, 2003, <www.businessweek.com/print/magazine/content/03_28/b3841091.htm?>.

"More Delicious Delicacies, Thanks to Tech," Business Week on line, pp. 1-3, retrieved Jul. 18, 2003, <www.businessweek.com/print/technology/content/jul2008/tc2003078>.

"Food Scientists to Assess Bioterrorism Risk," Reuters, Jul. 15, 2003; at <www.reuters.com>, retrieved Jul. 15, 2003, one page.

Hao Wu, William N. Hait, and Jin-Ming Yang, Small Interfering RNA-Induced Suppression of MDR1 (P-Glycoprotein) Restores Sensitivity to Multidrug-resistant Cancer Cells; Cancer Research, 63:1515-1516 (Apr. 1, 2003).

Raja Mishra, "Advances Begin to Tame Cancer," retrieved Jul. 6, 2003, <www.boston.com/dailyglobe/187/metro/advances; 5 pages.

Tony Strattner, "Genomic Advances of Past Decade are Real: Ordonez", Bio-IT World, <www.imakenews.com/health-itworld/e_article000165177.cfm?x=a1vsryl, avfsryl> retrieved Jul. 10, 2003 (3 pages).

Ouellette, Jennifer, "Biosensors: Microelectronics Marries Biology" The Industrial Physics, p. 11-12; 14; Sep. 1998 (c) American Institute of Physics.

Maggie Fox, "Cell-based Detector Lights up for Deadly Gems," Reuters, <www.reuters.com> retrieved Jul. 10, 2003, 2-pages.

Maggie Fox, "US Team Finds Hints of How, Why Cancer Spreads," Reiters, <www.reuters.com>, retrieved Jul. 12, 2003, p. 1-10.

Zuckerman, Laurie, "Taking the Guesswork out of Cancer Treatment Sicel Technologies," Business Leader, Sicel Technologies, 12(4):20 (Oct. 10, 2000). Abstract.

Anand Ramakrishnan and Ajit Sadana, "A Mathematical Analysis Using Fractals for Binding Interactions of Nuclear Estrogen Receptors Occuring on Biosensor Surfaces," Analyt. Biochem., 303:78-92 (2002), Chemical Engineering Department, University of Mississippi.

David Perlman, "Gene Variant Tied to Increased Susceptibility to Cancer, Research Finds Other Factors are Also Part of Equation," Wed., Aug. 6, 2003, <sfgate.com/cgi-bin/article.cgi?f=/c/a/2003/08/06/mn131526.dtl(p. 1-2).

Rhonda Ascierto, "Canary Chip Warns of Danger From Bioagents," <www.svbizink.com>; Fri., Jun. 20, 2003. (p. 1-2).

"Microarrays & Protein Chips Glossary," <www.genomicglossaries.com/content/printpage.asp?REF=/content/microarrays&protein> retrieved Jun. 27, 2003; (p. 1-20).

"Microarrays & Protein Chips Categories," <www.genomicglossaries.com/content/printpage.asp?REF=/content/microarrays&protein> retrieved Jun. 27, 2003; (p. 1-23).

"Sirna Therapeutics: RNAi," Sirna Therapeutics, <www.sirna.com/rnai/rnai.html>, retrieved Jul. 10, 2003.

Kricka, Larry J., "Miniaturization of Analytical Systems," Clinical Chemistry (1998) vol. 44, No. 9, pp. 2008-2014.

Schmidt et al., "Protein Sequence Comparison on the Instruction Systolic Array," LNCS (2001) vol. 2127/2001, pp. 498-509.

INTEGRATED BIOSENSOR AND SIMULATION SYSTEM FOR DIAGNOSIS THERAPY

CROSS REFERENCE

This is a continuation application for the U.S. pending application Ser. No. 10/646,682 filed Aug. 22, 2003.

BACKGROUND

1. Field of Invention

Invention relates to sensors and related software for monitoring or analyzing biological hosts or material.

2. Related Background Art

Various sensors are used to detect or measure macroscopic or molecular physiology in humans or other biological host. Additionally systems-biology software provides computational modeling of molecular structures and interactions for genomics, proteomics, metabolomics, transcriptomics, computational chemistry, pharmacogenomics, or other purpose. Such tools, however, are not easily or automatically integrated or reconfigurable for interdisciplinary diagnosis or therapy.

SUMMARY

Integrated biosensor-simulation system combines one or more sensor to detect various conditions in biological target or host, and software program or simulator using system-biology model and sensor data adaptively to provide therapy, diagnosis, or other automated feedback. Preferably one or more sensor is reconfigurable by the simulator. Optionally food material for consumption by the biological target is sensed for application to the simulator, which may apply certain regulatory condition. Switch couples simulator programmably to sensors.

DETAILED DESCRIPTION

Figure 1A:
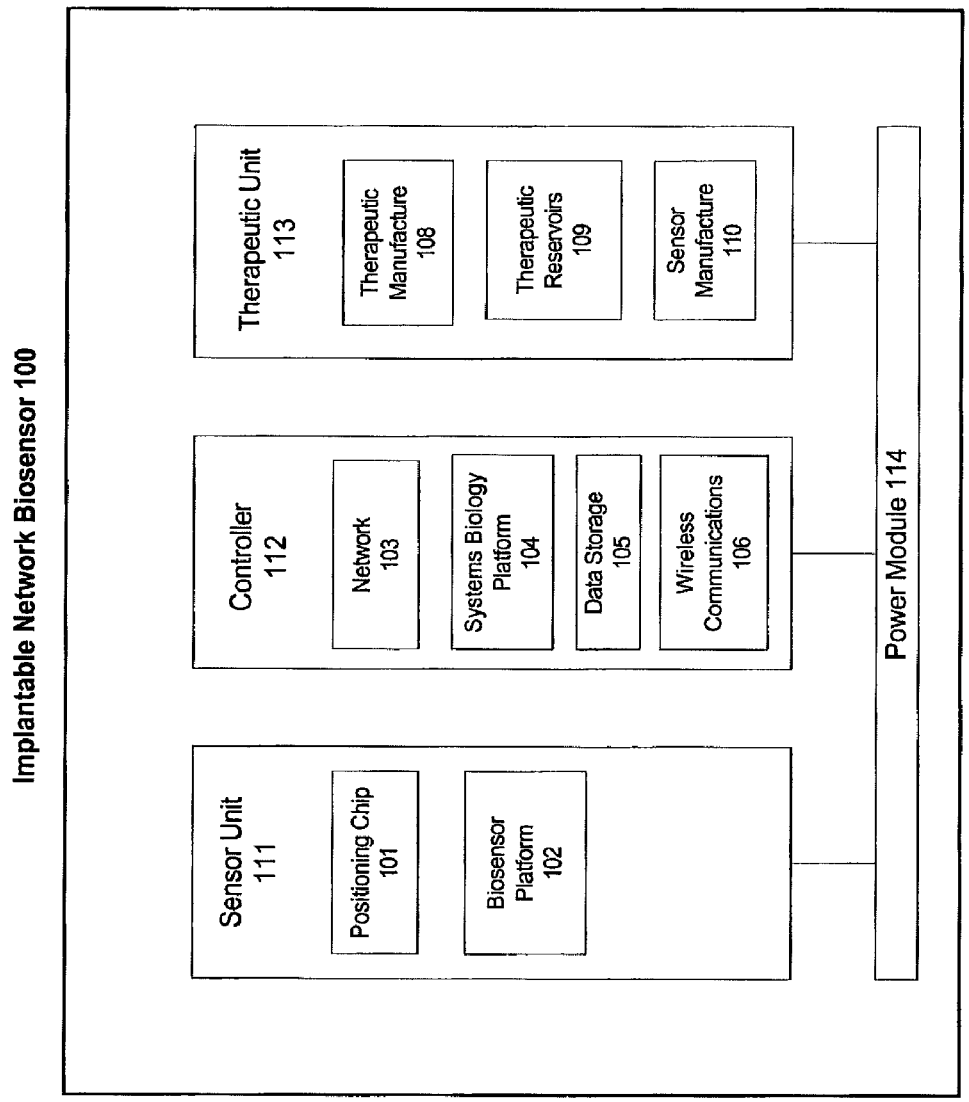
FIG. 1a shows sensor device according to aspect of present invention.

FIG. 1a architectural diagram illustrates implantable network biosensor 100. It is contemplated herein that sensor 100 may also operate without being implanted in biological host, but instead through external contact or attachment thereto. Optionally multiple coupled sensors 100 may provide fault-tolerant back-up or recovery facility, in case one or more sensors fails or malfunctions. Sensor 100 may be provided inside a host, e.g., mouth, larynx, blood vessel, vein, nose, ear, eye, heart, brain, lymph node, lung, breast, stomach, pancreas, kidney, colon, rectum, ovary, uterus, bladder, prostate, or other organ or using portable mobile application externally, e.g. skin, fingernail.

Sensor 100 includes sensor unit 111, controller 112, therapeutic unit 113, and power module 114. Sensor 100 components may be interconnected or communicate with other components using electrical, electronic, or electromagnetic signals, e.g., optical, radio frequency, digital, analog or other signaling scheme. Power module 114 provides electrical energy for sensor 100 to operate.

Generally biosensor 100 may sense individual genome, proteome, metabolism, transcription, translation, blood pressure, carbohydrate and oxygen concentrations, or other factors as described herein. Data is provided by sensor 100 to integrated network 103 that applies systems-biology software 104 to verify, model, or analyze, for example, relative sequences, 3-dimensional structure, molecular interactions, or overall cellular and physiological environment.

Systems-biology software 104 processes information and determines treatment dynamically for individual real-time physiological condition. Analysis report and other patient instructions are transmitted remotely as telemedicine service to network 103, which provides tasks to components, such as pharmaceutical or biopharmaceutical reservoirs 109, reconfigurable biosensors 102, wireless telemetry system 106, therapeutic manufacturers 108, or other applications.

Sensors 102 may be hardware-reconfigurable or software-programmable according to user or systems-biology programming or report instructions. Ongoing or intermittent scheduled or random sensing events occurs between therapeutic components and pre-programmed and reconfigured micro/nano biosensors 102, along with proactive or reactive feedback to patient or user from systems-biology platform 104. Preferably sensing process employs micro or nanoscale sensor 102 structure for minimal intrusion to individual health or physiology.

Optionally sensor system 100 provide wireless (RF) signal coupling with other sensors 100, such that communication occurs between different organisms having sensor 100. For example, sensor 100 may be implanted in pregnant host and another sensor 100 implanted in such host baby. Communication between sensors 100 may provide effective biological sensor signal transmission between separate hosts or organisms. Sensor 100 may be accessible according to IEEE 1451 network interface format.

Another example for multi-host communication implements sensors 100 for communication between separate related individuals, such as potential sexual partners, where one partner sensor 100 may sense sexually transmitted disease (STD) in such host, then such information is provided electronically to other host sensor 100 to produce proper antigens and antibodies to combat the STD.

Sensor unit 111 uses positioning device or chip 101 to position, locate or immobilize effectively target sample for analysis or sensing. The manipulated targeted sample comprises a biological molecule, organic or inorganic substance, such as cells, tissue, nutrients, chemicals, intracellular materials, extra-cellular materials, charged ions, pharmaceuticals, or molecular materials affecting host physiology.

Sensor unit 111 comprises multifunctional biosensor platform 102 for sensing and monitoring multiple biological materials, concentrations, inorganic or organic materials, cellular material, genetic material, nucleic acids, proteins, amino acids, peptides, antibodies, antigens, fatty acids, lipids, steroids, neurotransmitters, inorganic ions, pH levels, free radicals, carbohydrates, chemicals, small molecules, cells, tissue, pharmaceuticals, toxins, metabolites, or physiological levels macroscopically, microscopically, or nanoscopically.

Controller 112 uses network 103 to couple components for signal or data communication. Network 103 communicates data electronically to systems-biology platform 104. Controller 112 may be implemented using personal, desktop, server, notebook, mainframe, wireless portable or other computer or processing device having processor, digital memory and network or user interface.

Systems-biology platform 104 uses computer equipment, software programs or reconfigurable firmware or emulation logic devices to verify, model, simulate, or analyze stored or raw data using computational biology, such as bioinformatics, proteomics, metabolomics, pharmacogenomics or other analysis software or hardware tools. Systems-biology platform 104 interprets or integrates data from biosensor platform 102, and analyzes organism preferably as a whole on system level. Systems-biology platform 104 may be integrated within one or more integrated circuit, module or processor; or bilaterally communicate to outside non-host signal source through wireless communication unit 106.

Controller 112 may use data storage 105 for storing processed data or applications programs from systems-biology platform 104. Controller 112 includes wireless communication unit 106, allowing bilateral communication with outside source, which may access or control sensor unit 111, controller 112, or therapeutic unit 113 through wireless communication unit 106.

Network 103 may couple therapeutic unit 113 with controller unit 112. Therapeutic unit 113 includes therapeutic manufacture 108 for providing pharmaceuticals, biopharmaceuticals, bio-catalytic chips or devices, tissue, or physiological treatments. Biopharmaceuticals include biological material for therapeutic use.

Therapeutic unit 113 includes therapeutic reservoir 109, which provides micro or nano-scale reservoirs containing pharmaceuticals or biopharmaceuticals. Contents of therapeutic reservoirs 109 may be provided or configured before sensor 100 is implanted in or attached to organism, or may be manufactured and filled in vivo by therapeutic manufacture 108. Therapeutic reservoirs 109 may release or dispense contents when appropriately signaled by network 103.

Therapeutic unit 113 includes sensor manufacture 110 unit, which may provide additional sensors in vivo for additional targeted sensing or monitoring. Sensors from sensor manufacture 110 are part of or comprise biosensor platform 102.

Figure 1B:
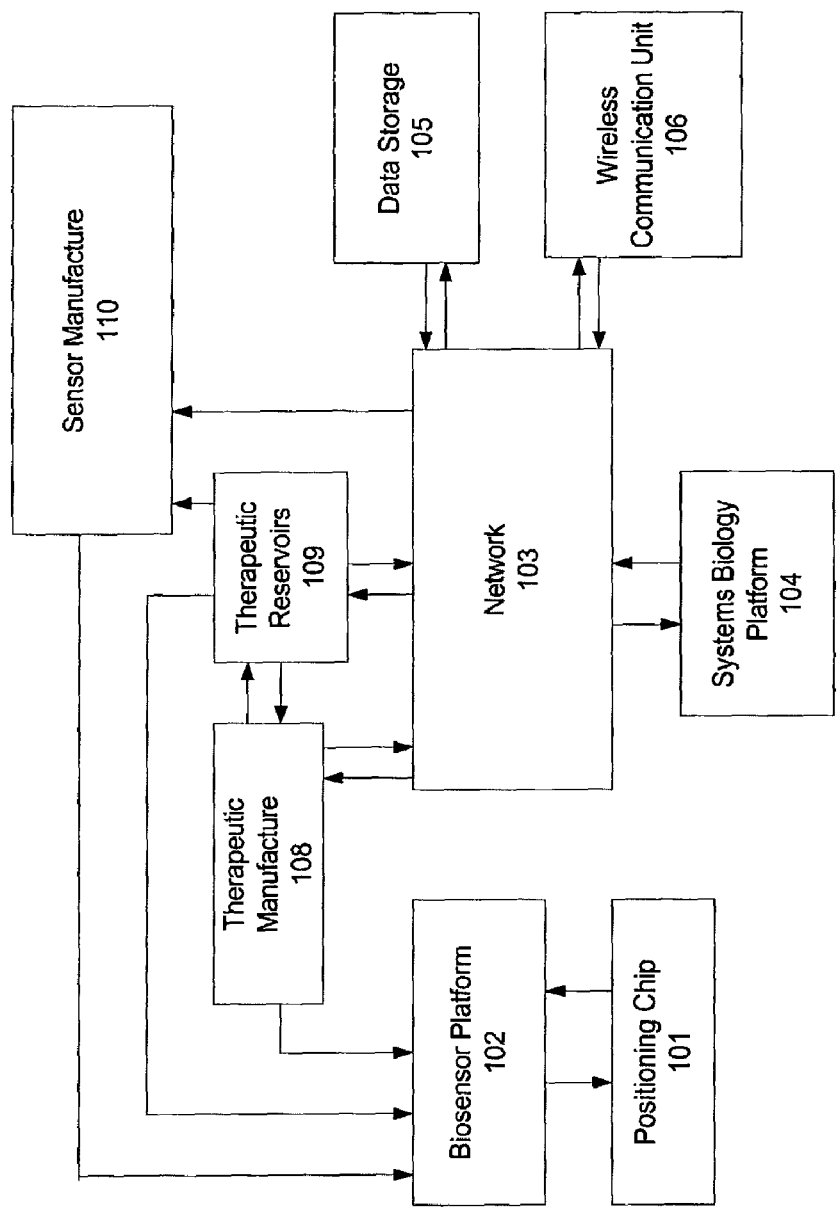
FIG. 1b shows sensor network according to aspect of present invention.

FIG. 1b shows positioning chip 101 for immobilizing or positioning target or tissue samples on or in sensor 102 for bio-sensing as described herein. Positioning chip 101 may use micro-fabrication, micro-fluidics, or microbiology to manipulate, sort, or prepare samples, reagents, or other biological entities for analysis, high-throughput assays, or diagnostic applications. Positioning chip 101 may accomplish sample placement using multi-channel patch clamp electrophysiology chip to control individual cells by applying current to cell ion channels, positioning cells onto planar patch clamp, for example, e.g., Aviva Bioscience technique. The cell is sealed on-chip and analyzed or broken, and intracellular materials extracted and analyzed; if the cell is not analyzed, cellular material may be positioned for analysis by diffusion, other natural technique, or through micro-fluidic manipulation.

Optionally positioning chip 101 comprises microelectronic array or microfluidic assay, including electrodes or biosensors in which at least one microelectrode or sensor cavity or element is capable of generating controllable electric current or voltage for drawing probes, samples, or reagents to locations on sensor platform 102, allowing faster, controlled hybridization or analysis.

Positioning chip 101 may use micro or nano-chips with nanoscale channels or membranes, e.g., iMEDD NanoPORE membranes. Depending on size of such membranes, pores selectively exclude antibodies or proteins, while allowing free exchange of glucose, nutrients, insulin, or other molecules. Positioning chip 101 may position mammalian cells of host organism, as well as bacterial, fungal, protozoan, or other unicellular or multi-cellular organisms for analysis.

Additionally positioning chip 101 may detect or collect micro-metastatic tumor cells circulating in the blood stream or other body fluids, including but not limited to nipple aspirate, cerebrospinal fluid, peritoneal wash, sputum or excrement such as urine and stool. Preferably enrichment of tumor cells from blood stream may occur in miniaturized or microelectromechanical (MEMs) version of device such as autoMACS to collect circulating carcinoma cells from blood of patients with urologic cancers, or similarly using nanoparticles conjugated with antibody to Epithelial Cell Adhesion Molecule to enrich for circulating tumor cells (CTC) of epithelial origin.

Further using positioning chip 101 in detection or collection, circulating prostate cancer cells in peripheral blood may be enriched, e.g., using technique by OncoQuick in Greiner, Germany, by using anti-human epithelial antigen paramagnetic microbeads or enrichment for disseminated breast cancer cells using advanced density gradient centrifugation; circulating endothelial cells serve as marker for vessel formation and vascular damage in cancer patients, such circulating cells being detectable for collection from peripheral blood using immunomagnetic beads coupled to antiCD146, an antibody raised against human umbilical vein endothelial cells.

Preferably collected tumor cells are analyzed on biosensor platform 102; for example, disseminated breast tumor cells may be analyzed by multiplex real-time RT-PCR (reverse transcriptase polymerase chain reaction) for mammoglobin, gabaII, B305D-C and B726P, or polymorphisms in carcinogen detoxifying UDP-glucuronosyl transferase UGT1A7 in blood of patients with cancer of proximal digestive tract. Also enriched, using anti-epithelial cells antibody Ber-EP4, e.g., Dynal Corporation technique, epithelial cells derived from peripheral blood of prostate cancer patients can be analyzed using nested RT-PCR-PSA (reverse transcriptase polymerase chain reaction prostate specific antigen) assay as sensor mechanism.

Biosensor platform 102 may employ twenty-five epithelial tumor cells in bone marrow and lymph nodes of esophageal carcinoma (pT1-3, pN0-1 and pM0) patients collected, using cytokeratin and EpCAM antibodies, respectively, by positioning chip 101 for micromanipulation in biosensor platform 102. Further DNA amplified by DNA sensor 201 using Mse-adapter PCR method may be analyzed by comparative genomic hybridization (CGH) for DNA-gains, -losses and point mutations by single-strand conformation polymorphism (SSCP). Also total RNA isolated PBMC in peripheral blood of breast cancer patients, may be subject to RT-PCR luminometric hybridization assay for presence of human telomerase reverse transcriptase, which is highly expressed in majority of tumor cells.

During sensing operation, positioning chip 101 may place samples on biosensor platform 102 for analysis. Biosensor platform 102 measures, detects, sequences, and other biological activities in serial or parallel in or out of organism. Biosensor platform 102 may use multi-functional high-throughput and density biochip having micro or nanoarrays, having substrates manufactured using glass, nylon, silicon, ceramic, metal, gel, membranes, synthesized nanomaterials, or other material.

Biosensor platform 102 provides data gathered from sensor arrays to network 103, which provides data to systems-biology platform 104, where data is integrated or processed. Systems-biology platform 104 may analyze empirically-sensed and simulated factors of individual organism in combination, to determine or confirm host profile of personal biological processes or makeup.

Systems-biology platform 104 may convey processed information to network 103. Network 103 communicates processed data to components coupled to network 103, including data storage 105, wireless communication unit 106, therapeutic manufacture 108, therapeutic reservoirs 109, or sensor manufacture 110.

Data storage 105 keeps records or stores processed data by systems-biology platform 104. Processed data from systems-biology platform 104, through network 103, optionally may be conveyed to wireless communication unit 106. Wireless communication unit 106 provides processed data access to external source, such as Global Positioning Satellite (GPS) receiver unit, media repository, personal computer (PC) or workstation, laptop, handheld computing device, cellular device, internal or external camera, another internal implantable or attached sensor or chip, external biological monitoring device, outside network, healthcare provider, pharmacist, insurance agent, or other device or service communicating with bio-sensor.

Processed data from systems-biology platform 104, through network 103, may be conveyed to therapeutic manufacture 108, where therapies are manufactured according to host biological status or simulation output. Effectiveness or side-effects of therapies, produced by therapeutic manufacture 108, are monitored by biosensor platform 102. Ongoing or intermittent feedback from biosensor platform 102, through network 103, to therapeutic manufacture 108 provides automated or iterative therapeutic process.

Optionally therapeutic manufacture 108 stores biological therapies in therapeutic reservoirs 109. Therapeutic manufacture 108 or therapeutic reservoirs 109 communicate through network 103 for filling or dispensing. Processed data from systems-biology platform 104, through network 103, may be conveyed to therapeutic reservoirs 109, where respective therapies are released according to biological status. Effectiveness or side effects of therapies, released by therapeutic reservoirs 109, are monitored by biosensor platform 102. For example, biosensor platform 102 may sense therapeutic effectiveness or side effects, while systems-biology platform 104 analyzes negative or positive effects to make recommendations. Ongoing feedback from biosensor platform 102, through network 103, to therapeutic reservoirs 109 provides automated or iterative therapeutic cycle.

Processed data from systems-biology platform 104, through network 103, optionally is conveyed to sensor manufacture 110. Sensor manufacture 110 comprises hardware or software-programmable (reconfigurable and software-programmable terms may be used interchangeably) biosensors in vivo that integrate into biosensor platform 102 for supplementary sensing. Sensor manufacture 110 may be used to monitor additional biological materials originally part of biosensor platform 102, as well as used functionally to replace damaged sensors. Sensor manufacture 110 may be used to sense newly-calculated operational conditions by systems-biology platform 104. Optionally sensor manufacture 110 may monitor interactions between novel drug therapies, produced by therapeutic manufacture 108, and organism biology.

Appropriate timing of functions is preprogrammed before biosensor 100 is attached or implanted into organism. Time intervals for sensing are programmed according to external diagnosis, which can range from seconds, minutes, hours, weeks, or longer. Once initial sensing begins, timing adjusts based on processed information by systems-biology platform 104. For example if genetic mutations within genome are found to be rare within multiplying cells, systems-biology platform 104 instructs biosensor platform 102 not to monitor genome as frequently.

Conversely if sensed or simulation parameter, input vector, stimulus, condition, environment or other host biological factor is changing frequently, or there is a high risk of change, then systems-biology platform 104 instructs biosensor platform 102 to increase frequency of particular sensor or assay. For example if organism changes through organ transplant, or is infected with new virus, systems-biology platform 104 instructs biosensor platform 102 to increase the monitor frequency of antigen or antibody responses while decreasing such factors that are relatively stable.

Figure 2:
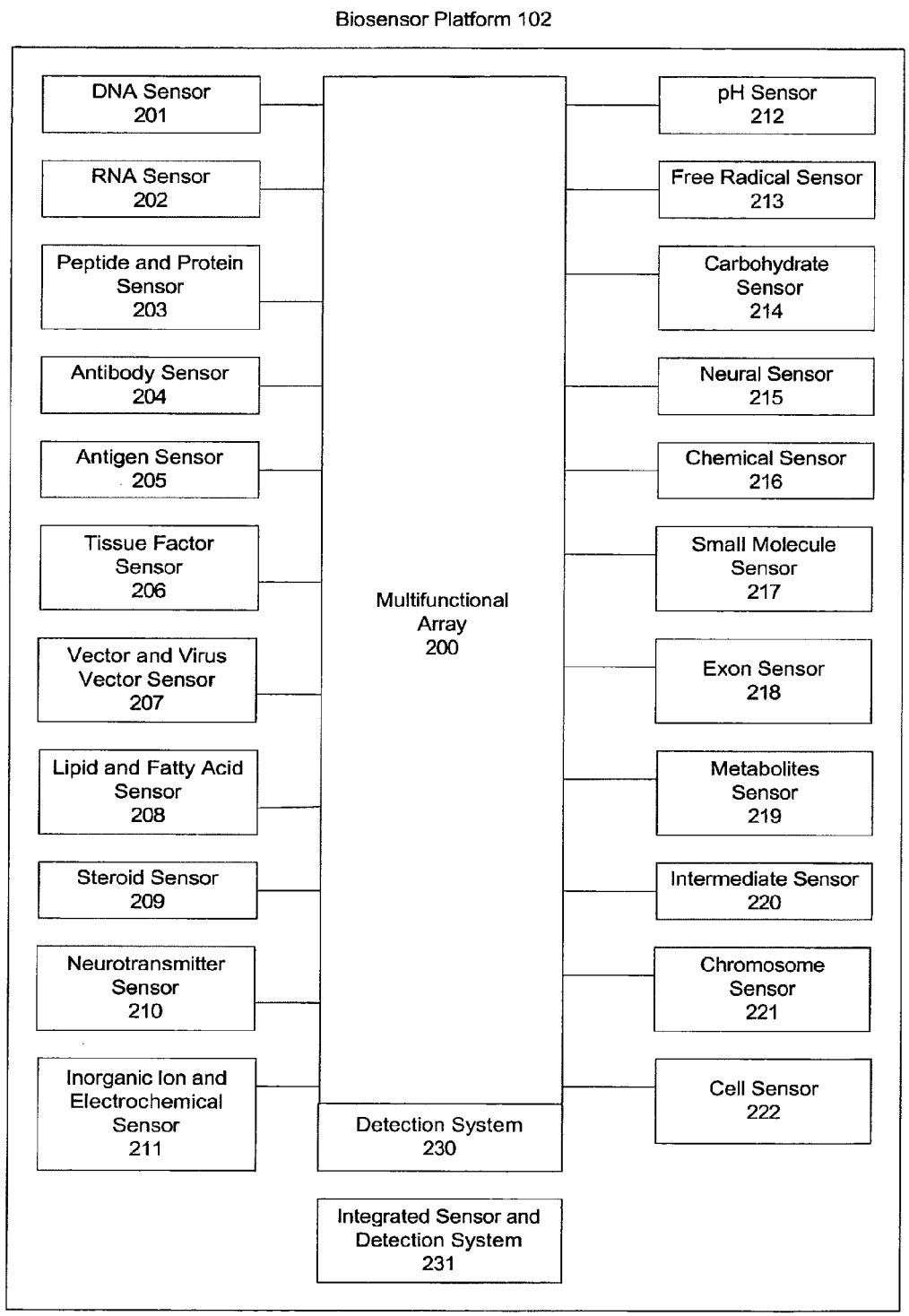
FIG. 2 shows sensor system according to aspect of present invention.

FIG. 2 shows biosensor platform 102 with multifunctional array 200 coupled to detection system 230, and integrated sensor and detection system 231. Multifunctional array 200 serves as programmable or logical interconnect for coupling or switching various sensor devices, and interacts with samples and detection system 230 interprets samples into data to be analyzed by systems-biology platform 104. Multifunctional array 200 may include micro and nanoarrays (M/N arrays) and biochips to test or monitor biological functions in particular organism.

Sensor components may include deoxyribonucleic acid (DNA) sensor 201, ribonucleic acid (RNA) sensor 202, peptide or protein sensor 203, antibody sensor 204, antigen sensor 205, tissue factor sensor 206, vector and virus vector sensor 207, lipid and fatty acid sensor 208, steroid sensor 209, neurotransmitter sensor 210, inorganic ion and electrochemical sensor 211, pH sensor 212, free radical sensor 213, carbohydrate sensor 214, neural sensor 215, chemical sensor 216, small molecule sensor 217, exon sensor 218, metabolite sensor 219, intermediates sensor 220, chromosome sensor 221, or cell sensor 222. M/N arrays are arranged architecturally as micro-electromechanical system (MEM) or as nano-electromechanical system (NEMS). This miniaturized architecture, as MEMS or NEMS device, allows multiple M/N arrays in a condensed form.

DNA sensor 201 is used to detect presence and/or sequence and/or structure of any DNA molecules including profiling for changes in methylation, monitor gene expression, undergo gene and DNA mapping, library screening, functional screen assays for nonsense and frame-shift mutations, scan the whole genome including micro-array-based comparative genomic hybridization to measure and map DNA copy number aberrations, detect disease markers, genotype single nucleotide polymorphisms (SNPs) including loss of heterozygosity analysis using SNP array hybridization and single-strand conformation polymorphism (SSCP), genotype organisms, examine protein-DNA interactions, and determine genetic characteristics individual to the organism.

DNA sensor 201 utilizes high-throughput M/N arrays for hybridization and use biochips, such as oligonucleotide M/N arrays, antibody M/N arrays, P1-based artificial chromosome (PAC) M/N arrays, bacterial artificial chromosome (BAC) M/N arrays, yeast artificial chromosome (YAC) M/N arrays, cosmid M/N arrays, cDNA M/N arrays, gene M/N arrays, whole-genome M/N arrays, SNP M/N arrays, gridded cDNA M/N arrays, Southern Blots, theme M/N arrays (array centered around a particular disease or gene family), bead M/N arrays (arrays made up of small beads containing capture oligonucleotides), bead based M/N arrays (arrays in which reactions take place on the surface of microbeads), gel-pad M/N arrays (arrays in which chemical and enzymatic reactions can be carried out on three dimensional pads, like miniature test tubes), microcantilever arrays (in which specific biomolecular interactions occur on one surface of a cantilever beam, such as changes in intermolecular interactions that generate sufficient surface stress to bend beam for optical detection, M/N gel electrophoresis chips and M/N arrays 2D gel electrophoresis chips, chromatographic protein M/N arrays, e.g., Ciphergen protein sensor, and hybridization techniques for deoxyribonucleic acid sensing. Phenotypic markers for DNA damage or repair include single-cell gel electrophoresis use comet assay in which DNA damage is visualized, e.g., Komet 4.0 by (Kinetic Imaging Ltd) Imaging System.

Optionally for single nucleotide polymorphism (SNP) detection, DNA sensor 201 may apply so-called invader platform, or other device for genetic sequencing of an individual. DNA sensor 201 can analyze peritoneal fluid from patients with ovarian cancer for loss of heterozygosity (LOH) at chromosomal arms 13 q (BRCA2 locus), 17 (BRCA1 and p53 loci) and 22q and for mutations in their p53 and k-ras genes. It can detect SNP (936 C>T) in 3' UTR of vascular endothelial growth factor gene (VEGF) in DNA extracted from blood of patients with breast cancer.

Further DNA sensor 201 can identify polymorphisms in carcinogen detoxifying UDP-glucuronosyl transferase UGT1A7 in blood of patients with cancer of the proximal digestive tract. Also methylation abnormalities in the promoter CpG islands of p16, HOX A9, MAGE A1 and MAGE B2 can be detected in sputum of lung cancer patients with DNA sensor 201. Sharply-elevated levels of stool DNA can be detected by DNA sensor 201 in patients with colorectal cancer. Stool DNA of surface epithelial cells is quantified using Picogreen fluorimetry.

DNA sensor 201 can detect chromosomal aneuploidy in cervical intraepithelial neoplasia or dysplasia using interphase cytogenetic technique called dual-color fluorescence in situ hybridization (FISH) targeting chromosomes 1, 7, 9 and 17 in Pap-smear slides and a thin layer of cervical cells.

Using DNA sensor 201, nipple aspirate fluid (NAF) containing epithelial cells shed from the breast ductal system can be analyzed. Extracted NAF DNA can be PCR amplified and analyzed for loss of heterozygosity in nuclear genome and deletions in mitochondrial genome using microsatelite markers and primer pairs, respectively.

Further DNA sensor 201 can be used to detect acute lymphoblastic leukemia prenatally by analyzing fetus blood to detect TEL-AML1 by FISH and genomic breakpoints by long-distance PCR. Using DNA sensor 201 and genomic DNA from whole blood, germ line polymorphism in KLK10 at codon 50 (GCC to TCC) associated with risk of occurrence in prostate cancer can be detected.

Also using DNA sensor 201, epigenetic changes, such as changes in GSTP1 methylation associated with prostate cancer can be detected in bodily fluids, e.g., urine and plasma, of prostate cancer patients. This detection uses real-time quantitative MSP and conventional MSP.

Further DNA sensor 201 is used to search for pieces of DNA in blood that are abnormally long, which is a signature of dying cancer cells; this test can be used for early diagnosis for patients with gynecologic and breast cancers. Optionally oligonucleotide array-based genotyping platform, such as Perlegen, is used for accelerated SNP analysis, allowing whole-genome scanning by DNA sensor 201.

RNA sensor 202 may be used to detect presence, sequence or structure of RNA molecules, such as spliced and un-spliced RNA, mRNA, tRNA, rRNA, improperly transcribed RNA, properly transcribed RNA from diseased DNA sources, ribozymes, RNAi mechanism and application in relation to cancer therapy, or changes or differences in mRNA levels, or structures made of ribonucleic acids. RNA sensor 202 utilizes high-throughput M/N arrays for hybridization techniques, inclusive of DNA sensor 201. Probes may be made to hybridize with RNA molecules, and Northern blot may be used in place of Southern blot technique.

RNA from enriched epithelial cells using anti-epithelial cells antibody Ber-EP4, e.g., per technique by Dynal Corporation, derived from peripheral blood of prostate cancer patients is analyzed for using nested RT-PCR-PSA assay by RNA sensor 202. Further, RNA sensor 202 can be used instead of second-look laparotomy in women with ovarian carcinoma treated with surgery and chemotherapy and show no sign of disease. Processed peritoneal washings are analyzed by telomerase repeat amplification protocol (TRAP) assay to detect residual disease. Total RNA isolated PBMC in peripheral blood of breast cancer patients, subjected to RT-PCR luminometric hybridization assay for presence of human telomerase reverse transcriptase that is highly expressed in majority of tumor cells.

Peptide or protein sensor 203 is used to detect primary, secondary, tertiary, or quaternary structures or activity of amino acid-based structures, such as sequence, enzymatic activity, protein function, interactions with agonists and antagonists, interactions with organic or inorganic structures or molecules, interactions with membranes, folding and enzymatic changes resulting in external factor, such as temperature, pH, ion concentrations, etc., N or C terminal characteristics, prions and misfolded proteins, amount and concentrations of proteins, bound and unbound state of proteins, sub-cellular localization, phosphorylated and dephosphorylated states, stages of degradation by proteases, stages of translation, gene and protein expression levels, e.g., using techniques such as ANTIBIOMIX (Milagen, Inc.) or Antigen Retrieval (Biogenex Laboratories, Inc.), protein-protein interactions, protein-small molecule interactions, protein-antibody interactions, protein mutations due to transcription and translation mistakes, or measurable factors associated with amino acid based structures. Sensor 203 may be implemented using electrophoresis tag or microassay to identify protein or gene simultaneously, e.g., Aclara eTag assay (Mountain View, Calif.).

Peptide or protein sensor 203 utilizes high-throughput M/N arrays for hybridization and use biochips, such as protein M/N arrays, proteome M/N arrays, whole-proteome M/N arrays, electrospray fabricated protein M/N arrays, gene expression M/N arrays, reverse transfection M/N arrays (for example membrane proteins that are difficult to purify), functional protein M/N arrays, Western blotting, microcantilever arrays, or quantitative and qualitative high-throughput techniques for amino acid entities.

Peptide or protein sensor 203 can be used to detect proteins in cerebrospinal fluid of patients with primary brain tumors.

Differentially-expressed proteins in processed CSF are digested and peptides identified by mass spectrometry. Presence of tumor-related proteins such as VEGF and VAV signifies presence of a primary brain tumor (179). Sensor 203, like SELDI protein-chip, similarly may be used to identify sixteen protein biomarkers in urine of bladder cancer patients, or instead of second look laprotomy in women with ovarian carcinoma who have been treated with surgery and chemotherapy and show no signs of disease. Processed peritoneal washings may be analyzed for telomerase activity to detect for residual disease.

Protein or peptide sensor 203 may be used in detection of diminished levels of N-CAM of <130 kDa in human serum of patients with brain tumors and the 80 kDa form associated with glioma. Further, protein and peptide sensor can be used in diagnosis of breast cancer by analysis of nipple aspirate fluid (NAF). Using SELDI-TOF capability, the presence of peptides at 4233.0 Da and 9470.0 Da is associated with cancer and the presence of 3415.6 Da and 4149.7 Da may be expected for normal samples. Thus sensor 203 can differentiate between diseased and unaffected populations.

Similarly protein sensor 203 may be used in breast-cancer diagnosis by analysis of serum samples. Samples applied to metal affinity capture chips activated with $Ni^{2+}$. Using SELDI protein chips/mass spectrometry feature and software to detect selected discriminatory peaks separate cancer from non-cancer groups.

Using same features of sensor 203, serum is analyzed to differentiate between hepatocellular carcinoma (HCC) and chronic liver disease (CLD), where α-fetoprotein fails as biomarker. Detecting 151 potential biomarkers in this way, system can provide diagnosis method for HCC. Using protein sensor 203 in diagnosis of prostate cancer, protein of 50.8 kDa can be detected in serum even where PSA levels are <4 ng/mL.

Further protein sensor 203 may be used in diagnosis of colorectal cancer detecting elevated HER-2 levels using standard ELISA and immuno-histo-chemistry (IHC) techniques. Elevated levels of secreted urokinase-type plasminogen activator (uPA) can be detected by sensor 203 in serum for diagnosis of pancreatic cancer using sandwich ELISA or similarly, elevated levels of kallikrein 10 in serum for diagnosis of ovarian cancer, or elevated levels of basic fibroblast growth factor (bFGF) in nipple aspirate fluid in diagnosis of breast cancer, or elevated levels of fibroblast growth factor-2 and pleiotropin in serum for testicular cancer diagnosis or interleukin 6 in the serum of hormone-refractory breast cancer patients using immunoassay.

Antibody sensor 204 may be used to detect monoclonal or polyclonal antibodies. Similar to above sensors, hybridization with M/N arrays may be used. Probes may be chemical or molecular biological material that hybridize to targeted antibody, such as DNA, RNA, peptide, protein, small molecule, steroid, or lipid. Microcantilever arrays and other binding techniques can be applied.

Antibody sensor 204 may use so-called phagotope biochip to display phage with epitopes that react with antibodies in sera of patients with ovarian cancer, or other cancers. Also presence of elevated levels of anti-survivine autoantibody in serum of head or neck cancer patients is detected by antibody sensor 204 using recombinant protein survivine as antigen.

Antigen sensor 205 may be used to detect or recognize individual immune response factors. For example antigen sensing may detect autoimmune response factors, such as sensing multiplex character autoantibody response in systemic lupus erythematosus, rheumatoid arthritis, or multiple sclerosis. Another example of antigen sensor 205 application may be identification or targeting of cell surface antigens for cancer therapy, e.g., Genentech approach.

Antigen sensor 205 may be used for early diagnosis of lung cancer or efficacy of chemotherapy by detecting nucleosomes in serum using assay, e.g., Cell Death Detection ELISAplus (Roche Diagnostics). Further antigen sensor 205 may detect tumor-associated antigens such as CYFRA21-1 for non-small cell lung cancer, and CEA, NSE and ProGRP for small-cell lung cancer.

Other sensing techniques for cancer detection contemplated herein include anti-malignin antibody screen test and tests for cancer markers including alpha fetoprotein (AFP), CA 15.3, CA 19.9, CA125, carcinoembryonic antigen (CEA), EVP test for epstein bar virus, T/Tn Antigen test, TK-1 test and prostate specific antigen (PSA) or free PSA (fPSA) test. For bladder-cancer bladder-tumor-associated antigen test (BTA), BTA stat test, BTA TRAK test, fibrin/fibrinogen degradation products test (FDP), and NMP22 assay. Protein-based markers may illuminate and map abnormal cells, e.g., Inpath system. Other blood tests include CBC blood test, biological terrain assessment (BTA), Pre-Gen 26, telomerase test or DR-70 test.

Tissue-factor sensor 206 may use tissue factor M/N array to sense tissues, tissue factors, or tissue origin, using probes or antibodies to hybridize with targets. Tissue-factor sensor 206 may detect increase in prostaglandin $E_2$ production in cells that over-express COX2. This detection is associated with enhanced growth, migration and invasion as in bladder tumors.

Lipid or fatty acid sensor 208 may provide membrane mapping, M/N gel electrophoresis chips and M/N arrays 2D gel electrophoresis chips, detergent analysis, M/N array analysis of glycolipids and membrane proteins, membrane fluidity analysis, cholesterol analysis, or other test to examine cellular or intracellular organelles lipid bilayers.

Lipid or fatty acid sensor 208 may detect changes in exposed membrane; for example, such sensor 208 may produce antibody, with traceable label conjugated thereto, to anionic phospholipids (AP), such as phosphatidylserine, phosphatidylinositol and phosphatidic acid, that are more specific for AP than annexin V. When released into blood stream this antibody binds activated, by inflammatory cytokines, hypoxia, hydrogen peroxide, thrombin or acidic conditions, endothelial cells and thus, tumor blood vessels have increased exposure of anionic phospholipids on their surface. Localization of label enables localization of tumor.

Lipid or fatty acid sensor 208 may detect levels of accumulation of synthetic membrane-permeable alkyl-lysophospholipids (ALPs), such as Edelfosine, Mitelfosine and Perifosine, that are anticancer agents that interfere with lipid mediated signal transduction.

Vector or virus vector sensor 207 may use microarray or assay with known sequenced virus attached, e.g., DeRisi Laboratory. Unknown viruses may be detected through examining homology to known viruses, and subsequent arrays can be manufactured by sensor manufacture 110 to detect new viruses. Optionally assays that detect homologs can be applied, such as Celera Diagnostic Viroseq™ HIV system for detection of mutations in human immunodeficiency virus (HIV) genome that confer drug resistance. Optionally assays for virus RNA can be used, such as Bayer Diagnostic Versant® HIV-I RNA 3.0 Assay for qualification of HIV-I RNA in plasma of infected people.

Further microparticle enzyme immunoassay (AxSYM HbsAg V2), e.g., Abbott Laboratories, may be used in quantifying reactivation of HBV during chemotherapy for lymphoma with Doxorubicin along with real-time quantitative PCR specific to region of major S protein. Virus and virus vector sensor 207 may be used for detection of oncolytic virus replication in tumor tissues.

Steroid sensor 209 detects levels of steroids in the body, and monitors or controls levels of steroid hormones. Sensor 209 targets hormonal changes associated with puberty, menopause as well as fitness-conscious steroid-pumping athletic types.

Neurotransmitter sensor 210, small molecule sensor 217, or exons sensor 218 detects using M/N arrays, such specific antibodies as probes that hybridize with desired targets. Inorganic ion or electrochemical sensor 211 may detect ionic concentrations using techniques, using MEMS technologies with dielectric currents, microfluidics, or dialysis on a N/M platform. pH sensor 212 may read pH by detecting $H_3O^+$ concentrations like silicon oxide pH sensors, e.g., Intelligent Pill. Free radical sensor 213 may be used to measure free radical activity, by using antioxidants as probes.

Carbohydrate sensor 214 may use oligosaccharide arrays, polysaccharide arrays, or carbohydrate chips, e.g., Glycominds glycochip, to measure glycan-protein interactions such as enzymes, antibodies, and lectins. Branched carbohydrates may bind to lectins involved in cell adhesion and migration processes. Also, natural branched carbohydrate like Lewis y, which is over-expressed in, for example, colon and ovarian cancer may be detected by carbohydrate sensor 214. Such sensor 214 may apply to whole blood glucose (WBG) monitoring system, or continuous glucose monitor, e.g., Sensors for Medicine Science.

Neural sensor 215 measures action potentials or voltage between neurons in central nervous system, using thin-film M/N electrodes as front-end sensors in MEMS and NEMS.

Chemical sensor 216 senses native or foreign chemicals, such as toxins, pharmaceuticals, vitamins, minerals, or other organic or inorganic chemicals. Chemical M/N arrays may be used, in which arrays of small organic compounds may be used to analyze interactions of proteins with various compounds. Conversely proteins or RNA may be used as probes to detect chemical substances.

Chemical sensor 216 may measure levels of carcinogen, benzo(a)pyrene diol epoxide, a metabolic product of benzo(a)pyrene found in tobacco smoke, known to cause 9p21 aberrations in peripheral blood lymphocytes in bladder cancer cases. Further chemical sensor 216 may measure tobacco-specific carcinogen 4-(methylnitrosamino)-1-(3-pyridyl)-1-butanone (NNK) that can induce transformation of human breast epithelial cells, and may be directly related to initiation of human breast cancer in smokers.

Metabolites sensor 219 uses protein or antibody M/N arrays that hybridize to particular metabolites. Sensor 219 is useful to detect excessive buildup of metabolites. For example metabolites sensor 219 can measure serum homocysteine levels, associated with increased risk of cervical cancer, and further DNA sensor 201 may detect common polymorphisms in one-carbon metabolic pathway; examples of such mutations include MTHFR C677T, MTHFR A1298C and MTR A2756G. Increasing copies of MTHFR 677 variant polymorphism is associated with increased homocysteine levels whereas increasing copies of MTR 2756 variant polymorphism is associated with decreased levels of such metabolite.

Intermediates sensor 220 uses various protein and antibody M/N arrays that hybridize to particular intermediates. Sensor 220 is useful to detect excessive buildup of intermediates; also sensing specific sequence, tertiary or quaternary structure of intermediates is used in drug design specificity.

Chromosome sensor 221 senses abnormalities in folding of chromosome, such as faulty histones, senescence-associated heterochromatic foci, or SAHF, since genes contained in these chromosomal regions are switched-on in proliferating cells, but are switched-off or "silenced" during cellular senescence.

Cell sensor 222 attaches whole living cells as probes, and is used for interactions with whole cells, such as cytotoxicity, drug metabolism, pharmacokinetics, target validation, interactions with other cells, extracellular materials, phenotypic analysis of genes and interfering RNA, as well as other biomolecules and compounds, e.g., Excellin Life Science bionic chip, which provides cell growth on chip. Effectively the cell becomes part of the chip, which allows manipulation and analysis of cell using microelectronics; the chip sends electrical signals through an on-board living cell, which detects changes in cell-membrane structure. The bionic chip can monitor and detect conditions that can cause cellular damage.

Optionally image cytometric measurement of breast fine needle aspirates can be used in cell sensing to predict nodal involvement in breast cancer. DNA ploidy, S-phase fraction, G0G1/G2M ratio, and minimum (start) and maximum (end) nuclear pleomorphism indices (NPI). Further cytometric imaging allows differentiation between normal cells in which PML protein resides in discrete PML bodies and promyelocytic leukemic cells in which PML protein is genetically rearranged or dispersed throughout the nucleus.

Sensor unit 111 may measure or transmit blood pressure, flow rate or other sensor data wirelessly to controller unit 112, similarly to so-called cardioMEMS devices for monitoring pressure within aortic aneurysm. Biosensor 100 is implanted using catheter and transmits data to controller unit 112. Optionally such device can be used assessing circulation to organ after transplant or reconstructive surgery. This provides physician with early indication of whether surgery is successful and prevent irreversible damage to organ.

Biosensor 100 may use implantable blood-flow monitoring system for providing synchronized blood vessel flow or myocardial wall contractility data to external monitor independent of transcutaneous leads. Further, since heart failure (HF) status of a patient is determined based on morphology of signal representative of arterial pulse pressure, the signal can be plethysmography signal that is produced by implantable or non-implanted sensor.

Time-derivative sensed signal may be produced based on signal representative of arterial pulse pressure; time derivation signal can be used to determine maximum and minimum peaks of signal representative of arterial pulse pressure. HF status can be assessed directly from time-derivative signal.

Biosensor 100 can be implanted using placement catheter, endoscope, or laparoscope; such device can be secured in LV or heart wall, e.g., using corkscrew, helical anchor, harpoon, threaded member, hook, barb, fastener, suture, or mesh or coating for receiving fibrous tissue growth.

Biosensor 100 provides less-invasive chronic measurement of left ventricular blood pressure or other parameters. Biosensor 100 can perform cardiosaver function to indicate to human subject that myocardial infarction is occurring; data is transmitted wirelessly to controller unit 112 for systems-biology analysis. Therapeutic reservoir 109 can inject thrombolytic or anti-thrombogenic agent into bloodstream promptly to dissolve thrombus that caused myocardial infarction, and prevent formation of additional thrombi.

Biosensor 100 may sense impedance measurements of heart, respiratory or patient motion, and from these measurements, generating alarm signal when measurements indicate occurrence of cardiac arrhythmia. Optionally rate-responsive pacing system includes sensor of minimum oxygen content in right atrium over prescribed time interval, and using such minimum oxygen content as control parameter for adjusting rate of pacemaker.

Optionally for sensors in multi-functional array 200, nanoparticles that specifically bind to particular molecules can be used to detect sequence, folding, binding, interactions, function, or overall characteristics. Once bound to particular biological molecules, arrangement of distances between nanoparticles results in different observable properties, such as color or pattern.

Array 200 may be configured electronically by systems biology platform 104 to couple or interconnect selectively according to simulation or modeling to access actual host condition via one or more biosensor signals. Such sensed signal set may be compared by simulator against model or other software prediction to confirm host or target material health or other problem, as described herein.

Nanoparticle arrangement on biological molecules provide or indicate function, e.g., Northwestern University DNA-Driven Assembly of Biomaterials system. By attaching gold particles to DNA nucleotides, DNA hybridizes with complementary strand and creates specific arrangement of gold particles. That arrangement of nanoparticles gives detectable color or pattern, which can be detected by optical device, and DNA can be sequenced.

Measuring color differences between nano-particle arrangement can also be applied to other biological molecule, e.g., Northwestern University Nanoscale Bioassay for Specific Antibodies. Rather than engineering nanoparticles that attach directly to the biological molecule, nanoparticles can be attached to specific antibodies. Binding of antibodies to targeted protein, DNA sequence, small particle, lipid, chemical, or other biological produces a particular color that is detectable or analyzable.

Also Nanoplex Technologies Nanobarcode Particles, made of different metals attached to biological molecules for multiplexing bioassays use probes attached to alternating metals on Nanobarcode to hybridize with biological molecules; then current can be run through Nanobarcode to determine molecules that bind to probes.

Detection system 230 may produce data from hybridization M/N arrays and other analysis techniques, e.g., fluorescent scanners, laser scanning phosphorimagers, mass spectrometry, fiber optics, atomic force microscopy, parallel surface plasmon resonance imaging (allows direct analysis of binding events without need of reporter systems or tags), conclusive-induced dissociation (CID) mass spectra through electrospray ionization tandem mass spectrometry (ESI-MS) on triple or quadruple or ion trap mass spectrometers, real-time polymerase chain reaction (PCR), PCR, Fluoresecence in situ Hybridization (FISH), or charged coupled devices (CCDs).

Integrated sensor or detection system 231 may produce data from samples, without separating detection from hybridization or other technique. Optionally semiconductor-based M/N array can be used, e.g., CombiMatrix matriXarray; such array allows precise, digital control of electrochemical detritylation, including embedded sensor designed in semiconductor substrate, alternatively to conventional fluorescence technology. Hybridization with array sends direct electronic signals for analysis.

Another example of integrated sensor detection system 231 assay, can be GeneFluidics 3D micro-fabricated platform with embedded electrochemical sensor array. This platform conducts molecular analysis of raw DNA or protein samples, e.g., no PCR or immunoassays. Electrochemical detection of samples, such as whole blood, saliva, stomach acids, or other bodily fluids, uses current to measure electron transfer with current signal, associated with hybridized nanomolecules, e.g., ssDNA, hybridizable nanoparticles).

Biosensor 100 generally comprises biological microelectromechanical (bio-MEMs) sensor chip or detection or transducer device that may be implemented or computer-modeled for operation in silicon, silica, glass, polymer or other substrate or instrumentation cavity, beam, surface, channel, encapsulated molecules, membrane, quantum dot or nanocrystal (e.g., CdS, CdSe, CdTe, ZnSe, or other colloidal group II-VI semiconductor), matrix or array for single or multi-channel independent signal detection in two or three dimensions in vitro or in vivo.

For example, sensor 100 may serve as high-throughput and sensitivity bio-physical, pharmaceutical or chemical recognition probe or cartridge for identification and/or characterization of host tissue or serum DNA, RNA, nucleic acids, protein, lipids, carbohydrates, enzymes, aptamers or other biomolecular or signal reporter target or any interaction, mutation, mass or rate thereof. Also such sensor may provide integrated, monolithic, discrete, or distributed, reagent-based or reagantless, microfluidic lab-on-chip microbiology mass spectrometry, flow immunosensor (e.g., FAST monitor for food or water quality), microarray or microassay functions, such as growing virus, bacteria or other eukaryotic or prokaryotic cells in microcells, nucleotide hybridization, polymerase chain reaction, molecular imprinting, chemical synthesis, ligand fishing, phage selection and concentration, multicomplex formation, diffusion limited concentration, or challenging antibiotics for rapid target detection, antibody susceptibility determination, or affinity and kinetic analysis.

Biosensor 100 may be implemented in quartz crystal microbalance for detecting or monitoring physical or chemical associated mass change or dissipation rate. Also whole cell or host sensor detection method may sense radioisotope, fluorescence, colorimetric, electrochemical, chemiluminescence, or bioluminescence. Additionally molecular or lipid-layer membrane-based sensor may operate to report change in electrical ionic, e.g., Ion Channel Switch biosensor using alternating current or voltage.

Furthermore encapsulated molecules may employ probes encapsulated by biologically localized embedding (e.g., PEBBLE nanosensors for intracellular chemical sensing, which may be delivered via gene gun, picoinjection, liposomal delivery, or phagocytosis, use matrices of cross-linked polyacrylamide, cross-linked decyl methacrylate, and sol-gel silica) for $H^+$, $Ca^{2+}$, $K^+$, $Na^+$, $Mg^{2+}$, $Zn^{2+}$, $Cl^-$, $NO_2^-$, $O_2$, $NO^-$ and glucose detection; optionally encapsulated outer shell may be modified as configurable platform to target selectively specific biological locations or antibodies, such as including or excluding species variously reactive to passing through or filtered by the polymer membrane.

Biosensor 100 may recognize protein for antigen-antibody recognition, particularly by localizing or mapping protein residue epitopes. For example sensor contact at epitope-paratope interface functions via crystallographic analysis of one or more poly- or monoclonal or antigen-antibody complex. Also sensor 100 may detect cross-reactive binding with antiprotein antibodies using synthetic peptides as antigenic binding probe for free peptides or peptides adsorbed to solid-phase, conjugated to carrier or attached to synthesis support.

Additionally sensor 100 may detect cross-reactive binding decrease to identify critical residues in peptides via systematic residue replacement, as well as other protein-protein interaction, for example, between protease-inhibitor, antibody-antigen, enzyme-inhibitor, hormone-receptor, or signal transduction or transcriptional complexes. Protein sensing analyte may include fatty acids, maltose, biotin, $Ca^{2+}$, $Co^{2+}$, $Zn^{2+}$, $Cu^{2+}$, glucose, glutamine, or other organic serum or tissue material.

Biosensor 100 may immobilize or control orientation of biomolecular target binding or catalytic sites via adsoption, entrapment behind membrane or in polymer or sol gel, covalent coupling, surface-immobilized polymer, or other capture system. Sensor orientation control may be accomplished via covalent coupling with attached glycosides, generation of specifically-located thiol groups, use of antibody-binding proteins, avidin/streptavidin capture system, or use of tags with engineered antibody fragments.

Additionally sensor spatial control of surface immobilization may use soft lithography for substrate or surface patterning to introduce surface function, deposition control by physical placement, light-directed immobilization and patterning, or electro-chemical deposition control, for example, using elastometric polymer poly dimethysiloxane PDMS.

Also molecular imprinting polymer sensor may employ affinity sensor where response is produced by accumulation of template on sensor surface, receptor sensor where response is generated by change in polymer characteristic or induced by template interaction, or enzyme-mimicking sensor where response is generated according to change in environment induced by molecular imprinting polymer-mediated catalytic reaction.

Furthermore antibody-based sol-gel sensor may use competitive assay detection, where antibody is encapsulated in gel, sol-gel sensor is immersed in sample containing analyte concentration and known fluorescently labeled analyte solution, excess analyte is washed from gel, and fluorescence emission from remaining bound analyte is measured optically; displacement assay detection, where antibody is encapsulated in gel with pre-bound fluorescently-labeled analyte, and gel is removed from solution and fluorescence emission from undisplaced analyte is measured; and fluorescence quenching detection, where fluorescently labeled antibody is encapsulated in gel, which is immersed in sample, and bound analyte quences fluorescence from antibody tag.

Biosensor 100 may employ optical biosensor or transducer with various assay formats. Direct assay may not use label, and analyte surface binding is measured directly. Sandwich assay secondary antibody binds to surface-bound analyte molecule after analyte binding to sensor surface. Competitive assay enables binding-site competition on sensor surface, and low sensor signal is obtained for high analyte concentration.

Optical transducer sensor may use input grating coupler (e.g., bidiffractive grating coupler), prism coupler, planar or nonplanar, polarimetric, ion-exchange or deposited-rib, channelized or non-channelized waveguide or interferometer (e.g. Mach-Zehnder interferometer), as well as surface plasmon resonance sensor (e.g., BIACORE system) using prism coupler, resonant minor with vibro-stirrer (e.g., Iasys), evanescent wave fiber optic biosensor for multi-analyte detection (e.g., RAPTOR antibody identification system), displacement flow detector, or other optical or time-resolved or phase fluorescence transducer (e.g., to detect fluorophore-labeled binding protein or fluorescence resonance energy transfer), or fiber optic elements.

Biosensor 100 may employ acoustic transducer or wave device, such as bulk or surface acoustic wave device, thickness-shear mode resonator, shear-horizontal surface acoustic wave, acoustic plate mode, or love wave sensor, for example, to detect and characterize sensitive biological binding events in real time without labeling, by measuring energy loss occurring at liquid-solid biomolecular interface.

Biosensor 100 may employ fast-flow injection or microtiterplate immunoassay using enzymatic amplification electrodes, for example, via bi-enzymatic substrate recycling for signal amplification using electrochemical or bioelectrocatalytic redoxlabel immunoassay. Bioelectrocatalytic sensor electrode material for detecting phenolic targets via alkaline phosphatase measurement, for example, may include glassy carbon, graphite, carbon paste or ink, or gold.

Preferably sensing devices or techniques are provided or performed in miniaturized implantable format. However some sensor devices or methods may require sample from implanted device to be transferred to instrument located outside the body. Data generated by such instrument is transmitted to systems-biology platform 104 for analysis or modeling.

Biosensor platform 102 sensors, detection systems, or components may apply to parasitic or symbiotic organisms, such as bacteria, fungi, protozoa, plant, or other unicellular or multi-cellular organisms provided in host organism. For example DNA sensor 201 may sense DNA structure of fungus cell living within such organism, peptide or protein sensor 202 may read its protein structures, and other sensors may read other biological properties. This information along with data from host organism is interpreted with systems-biology platform 104, and solution to expunge fungi is calculated or implemented.

Figure 3A:
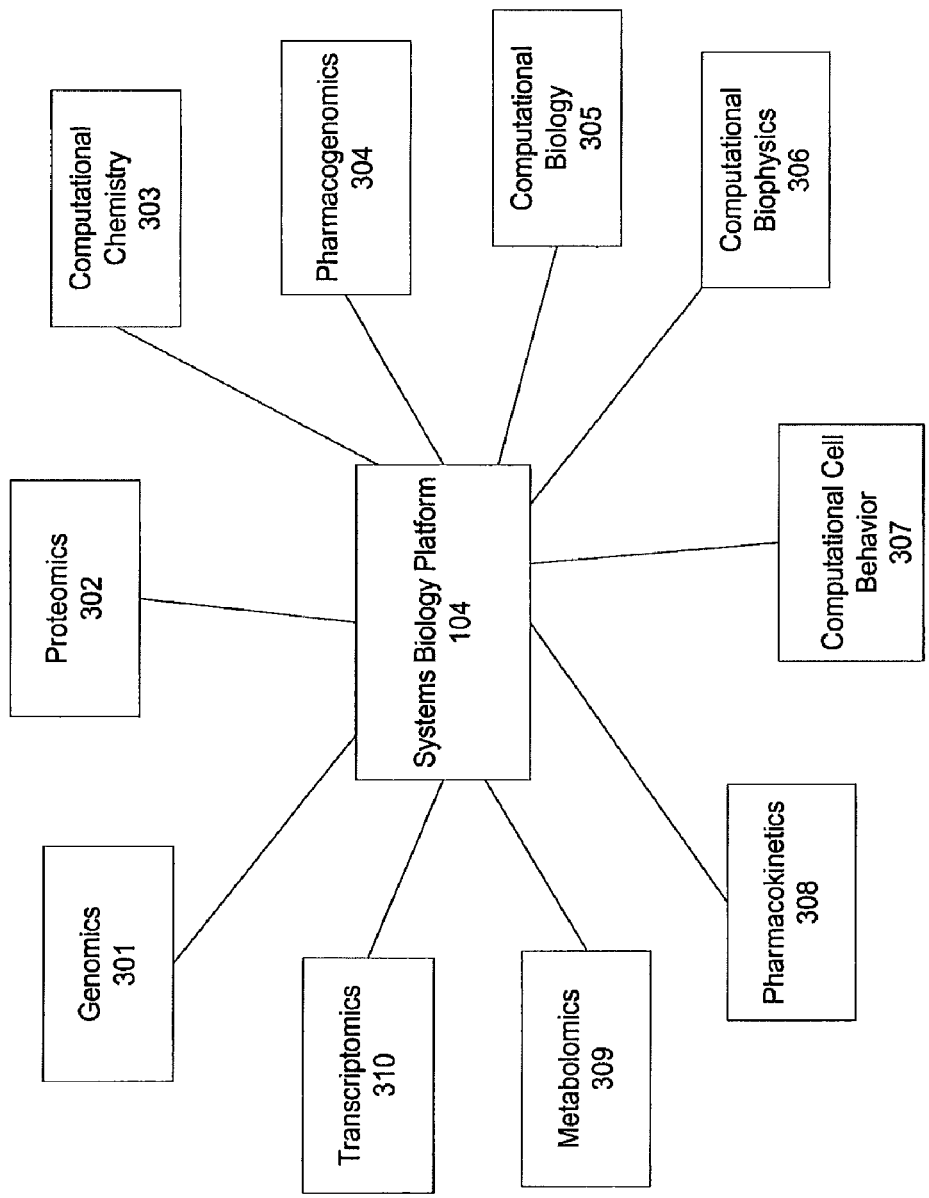
FIG. 3a shows systems-biology software according to aspect of present invention.

FIG. 3a shows software components of systems-biology platform 104. Once biosensor platform 102 produces comprehensive data on system, it is sent to network 103 and processed or analyzed by systems-biology platform 104.

Systems-biology platform 104 analyzes overall or partial structure of system or host, combining data from sensor components as well as model data of biosensor platform 102. Systems-biology platform 104 uses software for analyzing genomics 301, proteomics 302, computational chemistry 303, pharmacogenomics 304, computational biology 305, computational biophysics 306, computational cell behavior 307, pharmacokinetics 308, metabolomics 309, transcriptomics 310, bioinformatics 311, other computational behavior of the biological system, or other "omics" studies.

Other software may be integrated to understand or implement biological system on personalized level, e.g., specific gene sequence, individual protein interactions, personal localized mRNA levels, dynamics of particular system, methods of control, personal cytotoxicity, and methods to design and modify the system; comprehensive data set is generated to understand fully or partially subject organism.

Genomics 301 may map, sequence, analyze, or discover function of organism genome. Structural or functional genomics may be used in genomics 301. Proteomics 302 analyzes organism proteome, describing set of proteins expressed during lifetime of cell or group of cells. Proteomics 302 calculates structure determination, at lower level, to functional analysis, or cell modeling at higher level of modeling.

Computational chemistry 303 uses algorithmic tools to facilitate chemical analyses. Chemical analysis occurs at atomic or molecular level, examining how individual and groups of atoms, compounds, or other structures interact with living system; further it analyzes chemical relationships between biological structures.

Pharmacogenomics 304 calculates potential drug responses based on personalized genetic information. This information is useful for determining appropriate therapies or preventing adverse reactions.

Computational biology 305 uses algorithmic tools to facilitate biological analyses. Computational biophysics 306 uses algorithmic tools to facilitate biophysical or biokinetic analyses. Computational cell behavior 307 uses algorithmic tools to facilitate complete analyses of intracellular or intercellular behavior.

Pharmacokinetics 308 determines or predicts kinetic interactions between potential drugs and organism biological molecules, taking into account variable interaction factors, such as sterics, charge, dipole forces, or other factors that determine molecular interactions.

Metabolomics 309 analyzes organism overall metabolic profile, such as metabolism rates, amounts of metabolite intermediates, metabolic efficiency, structure of metabolic proteins, interactions between metabolic proteins and therapies, phosphorylative rates, or other aspects of individual metabolism.

Transcriptomics 310 analyzes organism transcription profile, such as efficiency, transcription errors to mRNA, intron-exon-splicing, biological transcription machinery, or other attributes of organism transcription.

Bioinformatics 311 undergoes database-management activities, involving persistent sets of data that are maintained in consistent state over indefinite periods of time. Bioinformatics 311 provides information content or flow in biological systems and processes; it serves as bridge between observations (i.e., data) in diverse biologically-related disciplines and derivations of understanding (i.e., information) about how systems or processes function, or subsequently the application.

Figure 3B:
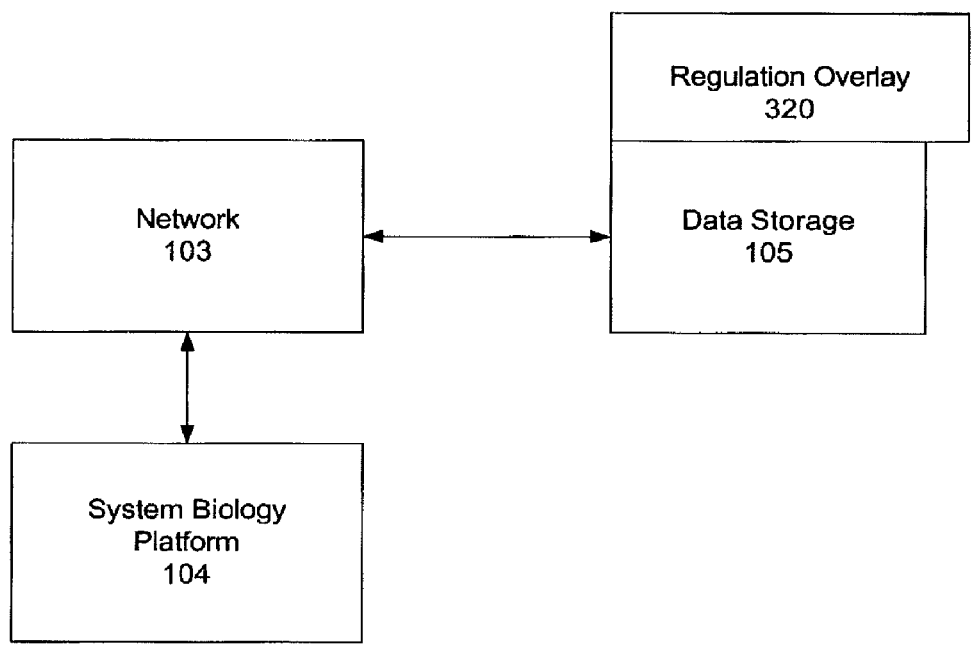
FIG. 3b shows systems-biology software and data according to aspect of present invention.

FIG. 3b shows ability to transfer information between systems-biology platform 104 and data storage 105 through network 103. This allows comparative studies between previously programmed and stored data with real-time computation; comparative studies serve as check against errors made by biosensor platform 102, and provide insights into overall systems understanding.

Also data storage 105 stores information processed by systems-biology platform 104. Data storage 105 may be located internally or externally relative to the organism, which can be accessed through wireless communication unit 106.

Regulation software or overlay 320 couples to data storage 105. When systems-biology platform 104 communicates with data storage 105, regulation overlay 320 assures that therapies, instructions, or other communications complies with Food and Drug Administration (FDA), Patent and Trademark Office (PTO), or other government regulatory bodies.

Regulation overlay 320 can store information or instructions for private agreements or regulations, such as contract or licensing agreement between biosensor 100 and pharmaceutical company. Depending on severity of organism condition or systems-biology platform 104 suggested therapy, communication directly or indirectly with FDA may be possible in instances where "expanded access," "compassionate use," "well characterized biological products," and other FDA exceptions apply. FDA may respond favorably and allow use of unapproved therapy (suggested by systems-biology platform 104) if exceptions apply.

Systems-biology platform 104 may implement neural network to model biological system or serve as decision aid for medical applications, problems or diagnosis. For example such platform 104 may employ methods as pattern recognition, feature extraction, supervised learning, unsupervised learning, or learning algorithms. Supervised learning methods may include Fisher's Linear Discriminant, Gradient Descent Procedures, Perceptron Algorithm, Relaxation Procedures, or Potential Functions for linearly separable sets, or Nonlinear Discriminant Functions, Hypernet, Minimum Squared Error Procedures (MSE), or Ho-Kashyap Procedure for nonlinearly separable sets.

For multiple category classification problems, supervised learning methods may include the Fisher Linear Discriminant, Kesler Construction, or Backpropagation. Unsupervised learning methods may include clustering, Kohonen networks, Kohonen Competitive Learning, Hebbian learning, Adaptive Resonance Theory (ART) or prototype distribution map (PDM). Clustering approaches may include Basic Isodata Procedure, similarity measure approach, or criterion functions.

Criterion functions approaches may further include sum of squared error criteria, minimum error criteria, or scattering criteria, and such criteria may be used in an iterative optimization procedure. Platform 104 may also employ clustering approaches such as hierarchical clustering or metrics.

To assist in medical decision-making, systems-biology platform 104 may implement artificial intelligence or decision techniques, particularly data-based techniques or knowledge-based techniques. Data-base techniques may include approaches such as database, decision theory, pattern recognition, or Bayesian analysis, while knowledge-based techniques may include mathematical modeling and simulation, symbolic reasoning, as well as databases.

Systems-biology platform 104 may employ database such as patient record structures (e.g., hierarchical databases, National Library of Medicine, MUMPS (Massachusetts General Hospital Utility Multi-Programming System), ARAMIS system, PROMIS (problem-oriented medical information system), or medical database management system (e.g. MEDUS/A)). Systems platform 104 may employ disease database (e.g. oncology, rheumatology), or decision-support system (e.g. HELP program).

Platform 104 may employ differential diagnosis database (e.g. RECONSIDER or DXplain), online database, radiological database (e.g. CHORUS (collaborative Hypertext of Radiology)), or Human Genome Project. Mathematical modeling and simulation may apply to modeling of organism or biological process. Biological process may be represented by mathematical equations and evaluated.

Simulation involves representation of organism or biological process on a computer. Mathematical formulation may apply to administration of drugs or analysis of drug toxicity or drug level in a biological system. Pattern-recognition techniques may include discriminant analysis, method of classification using Bayes' Rule, parameter estimation, supervised learning, or unsupervised learning.

Unsupervised techniques may include Parzen windworks, k-nearest neighbor estimation or other learning clustering techniques. Decision theory techniques may employ Bayesian analysis or Markovian analysis. Symbolic reasoning techniques may employ knowledge-based expert systems including early expert systems, second-generation expert systems. Techniques of expert systems may include knowledge representation, heuristic search, natural language understanding, and exact reasoning. Second-generation expert systems may employ causal models, reasoning with uncertainty, or hybrid systems.

Systems-biology platform 104 may implement fuzzy techniques, (e.g. fuzzy set theory, fuzzy logic, fuzzy variables, or membership functions) for use in neural networks and expert systems. In dealing with uncertainty in supervised learning networks, neural networks may further employ pre-processing of fuzzy input, propagation of results through the network, or interpretation of final results.

Propagation of results may employ max-min networks, learning algorithms for interval data, or analogue models. Unsupervised learning methods may employ fuzzy associative memories or fuzzy clustering. Fuzzy methods for use in clustering include relation criterion functions, object criterion functions, fuzzy isodata, convex decomposition, numerical transitive, generalized nearest neighbor rules, or HCM/FCM clustering algorithm.

Uncertain information in knowledge-based system may employ fuzzy techniques when dealing with uncertainty in relation to input data, knowledge base, inference engine (e.g., binary logic engines or fuzzy logic engines), evidential reasoning (e.g., possibility theory, probabilistic approaches, or Dempster-Shafer Belief Theory), compatibility indices, or approximate reasoning.

Alternatively systems-biology platform 104 may employ probabilistic systems or statistical analysis for analysis of medical data. Probabilistic systems may include Bayesian approaches, parameter estimation, discriminant analysis, statistical pattern classification, unsupervised learning, or regression analysis.

Bayesian approaches may include Bayes' Rule, Bayes' Decision Theory, risk analysis, supervised Bayesian learning, or decision trees. Parameter estimation may include maximum likelihood estimation or Bayesian estimation. Unsupervised learning may include Parzen window approach, nearest-neighbor algorithm, mixture densities and maximum likelihood estimates, unsupervised or Bayesian learning.

For example systems-biology platform 104 receives raw data from sensor unit 111 and employs neural networks, artificial intelligence, fuzzy systems, or probabilistic systems to aid in medical decision making for therapy recommendations or diagnosis.

Optionally additional information or test data helpful for diagnosis or treatment may be gathered from electronic files or user input from an outside source via and stored in data storage 105. Additional information or test data may include: patient age, height, weight, symptoms, allergies, diet, previous or present medications, medical or family history of disease, sickness or infection, results of previous blood, urine or other bodily fluid analysis, or other nongenetic (e.g., environmental) or immunological factors relating to the patient.

Optionally systems-biology platform 104 sends therapy recommendations or diagnosis report to an outside source via wireless communication 106 and store recommendations or report in data storage 105.

In clinical, managed-care, hospital, diagnostic, therapeutic, or biomedical application or embodiment, systems-biology platform 104, using one or more firmware, source or object code software, configurable logic chip or device, digital signal processor, systolic processing array, or other finite state machine, actually or effectively may compare set of bioinformatic values associated with sensor signal or simulation data, preferably associated with same or different temporal states, to determine or otherwise recognize one or more genomic mutation associated with or corresponding to target patient, animal, plant, or other biological host.

Furthermore systems-biology platform 104 may operate autonomously, in cooperation with other computer system nodes, clients, or processing elements, to collect, process and display various host or patient sensor or simulation data, preferably in combination.

For example patient information and other personal or medical record data may be received via questionnaire or otherwise retrieved, such as host identification, drug treatment, prescription, and dosage, single or multiple concomitant food or drug allergy, interaction or side effect, pregnancy, lactation, as well as bioinformatic, genetic, proteomic, metabolomic, and other monitored, simulated or sensed mutation-related data as described herein.

Systems-biology platform 104 may be used in time-critical emergency, urgent, or trauma situation to improve patient health-care diagnosis and treatment, for example, by early-detection, expediting and assisting physician, paramedical, nursing, or other professional analysis and treatment.

Sensed signal or simulated data as electronically may be labeled for indicating genomic mutation, significantly improves quality and accuracy of medication delivery and administration to identified subgroups of patients having certain adverse response to medication, food, or other treatment.

Additionally such data or signal may include pharmaco-genomic or pharmaco-kinetic clinical or indications based on genetic, proteomic, metabolomic (i.e., analysis of small organic cell molecules and metabolic response thereof), or other bioinformatic variant or mutation, or other genetic-based condition or profile (e.g., sex, race/ethnicity, etc.) such as drugs to be avoided, or considered as alternative. Thus optimally host susceptibility or predisposition to toxicity or other adverse host reaction or side effects to certain identified food, drugs, or other medical treatment may be minimized, mitigated, or eliminated using automated rule-based advise or expert system.

For example, systems-biology platform 104 may alert medical professionals when host patient is determined via sense or simulation approach to detect genomic mutation that patient ability to produce thiopurine S-methyltransferase (TPMT) enzyme activity is compromised. TPMT genetic test (commercially available from DNA Sciences (Raleigh, N.C.) enables identification of patient at risk for 6-MP/azathioprine/thioguanine toxicity, and improves confidence through tailored dosing regimens, while minimizing concern over drug-induced complication.

Alternatively, genomic mutation to G protein-coupled receptors (GPCR) molecular target and variant alleles may be detected to electronically label and thereby effectively modify host drug therapy. Another genomic mutation that may be detected and labeled is enzyme debrisoquine hydroxylase (CYP2D6), isozyme of microsomal cytochrome P450 monooxygenase system; encoding gene is located in CYP2D gene cluster in contiguous 45-kb region of chromosome 22. Here, at least nine polymorphisms of CYP2D6 affect metabolism of more than 30 different pharmaceuticals, including β-adrenergic receptor antagonists, neuroleptics, and tricyclic antidepressants.

Systems-biology platform 104 may couple electronically or digitally to hospital, physician, nursing, or other medical staff communication system to enable network-accessible prescription renewal, appointment scheduling, lab-result entry or retrieval, referrals to specialists and disease management, as well as generally computerized physician or pharmacy-ordering scheme, patient communications, access to medical simulation, test or sensor results, insurance claim status, and bar-coding of pharmaceuticals, and automated medication checks for possible errors.

System-biology platform 104 may employ simple identical or substantial equivalent value check between recently-measured value and previously-stored value for same host, for example, after host exposure to radiation or other carcinogenic sources. Such algorithm may be executed to adapt iteratively or dynamically in real-time or in multiple or parallel processors based on currently or recently-measured, monitored, or sensed host bioinformatic values, for example using fuzzy system, Bayesian or neural network, to improve compute or processing performance by comparing initially values that previously are known or recorded to be related or likely to be related or otherwise weighted to sensor signal or simulation data.

Additionally electronic access to sensor signal or simulation data may be restricted, secured, encrypted, or excluded unless the host thereof explicitly or voluntarily provides prior informed consent to access such information.

Hence, comparison serves to detect presence or absence of target sensor signal, simulation data or other genomic or bioinformatic value (e.g., oncogene, tumor suppressor gene, allele, enzyme, repeat sequence, micro-deletion, or other mutant gene product, protein, or metabolome) that causes, or increases or decreases risk of one or more host disease, disorder, syndrome, allergy, or other biological condition.

Such simulation data or sensor information may be stored in data storage 105 or in other digital storage accessible or otherwise retrievable through network 103. Such stored information may be formatted according to one or more conventional, industry-standard, or otherwise publicly or commercially-available software, processing, storage, and communications protocol, as well as databases for metabolic, signaling, regulatory and pathway data.

Additionally other genomic relational or object-oriented knowledge base or data sources may be network-accessed, such as GenBank, Unigene, LocusLink, Homologene, Ensemble, GoldenPath, or NCICB Cancer Genome Anatomy Project (CGAP). Such information may be accessed using ontology-based interfaces that are defined to be logically related, for example, using annotation format such as Distributed Annotation System (DAS).

Optionally systems-biology platform 104 data or instructions may be specified and otherwise annotated, such as hypothesis definition, experiment design, sample preparation and distribution, experiment run, data acquisition, result analysis, data mining, design refinement, modeling, knowledge discovery, or project report. Additionally such functions may be applied to simulation data or sensor signal processed by software or hardware analysis tools, e.g., for pharmacogenomics, gene expression, high-throughput sequencing, or proteomics (functional or structural) use-case domains.

Preferably such stored information complies, at least in part, with data exchange and management framework and specifications provided by Interoperable Informatics Infrastructure Consortium (I3C), which technical and use-case model documents, and recommended implementations, as described on-line at http://www.i3c.org/ are hereby incorporated by reference as appropriate herein.

For example, one or more I3C-compliant or recommended data format may be employed during operation of electronic label processor, as described herein. Accordingly simulation data or sensor signal may be accessed, and displayed or otherwise imaged using electronic display I/O hardware or software, for gel chromatography images, original data from biological arrays, arrays of time-series data from mass spectrometry, illustrative functional depiction of proteins, simple microscope images, patient records with medical images, derived data from multiple or time-series images, electrocardiograms, or original drawings and annotations to medical images made by examining professionals. On-screen search capability enables medical professional quickly to locate and interpret particular host simulation data or sensor signal, such as gene sequence, protein, enzyme, allele, or other related detail.

Network 103 access to various databases or other digital repository may couple in n-tiered architecture multiple client interfaces, serve components, back-end objects and data sources. For example, Linux-based, Netscape, or Microsoft Internet Explorer browsers or applications, e.g., based on Java, non-Java, Perl, C, C++, or other programming or development software, run on client nodes 60 may receive information, such as in various markup-language, e.g., HTML, XML, etc., from back-end objects over conventional network messaging or transport protocol, e.g., hyper text transfer protocol (HTTP), TCP Internet Protocol, simple object access protocol (SOAP), file transfer protocol (FTP), HOP, etc. Additionally Universal Description Discovery Integration (UDDI) registry and Resource Description Framework (RDF) agent advertising formats may be used.

Further genomic, proteomic, or metabolomic sequence analysis software tool, for example, (e.g., BLAST, TimeLogic) may be used by controller 112 to discover or characterize host genomic, proteomic, or metabolomic sequence, acquired and qualified from one or more sources, such as sensor unit 111 or data storage 105. Thus, internal and external sequence and protein libraries may be updated and maintained, certain redundant, unqualified or external data being filtered for internal sequence processing. One or more target, putative or otherwise mutant gene or bioinformatic value is then determined and cataloged effectively by systems-biology platform 104.

Hypothetical function of such determined gene or value may be generated manually, automatically, or homologously by finding similarity to known or other prior values. Genetic, proteomic, or metabolomic analysis protocols and similarity analysis may be defined and selected, thereby enabling or constructing functional hypotheses to be generated, prioritized, or reviewed using sensor measurements or other host evidence.

Proteolysis sample preparation may be performed (e.g., HPLC, gel electrophoresis), then mass spectroscopy or tandem MS analysis and compression, quantitization, and fragment size genome analysis for candidate prediction, proteome or metabolome comparison, and other quantitative analysis using modeling tools and databases.

Systems-biology platform 104 may receive data from sensor unit 111, and neural networks, artificial intelligence, fuzzy systems, or probabilistic systems consider presence of conditions in diagnosis of genetic disorders: point mutations, mutations within non-coding sequences, deletions and insertions, trinucleotide repeat mutations, autosomal mutations, gain of function mutations, loss of function mutations, mutations in mitochondrial genes, enzyme defects, defects in receptors and transports systems, defects in receptors and transport systems, alterations in structure, function or quantity of non-enzyme proteins, defects in receptor proteins, defects in protooncogenes or tumor-suppressor genes, aneuploidy, unbalanced autosome, sex chromosome abnormality, fragile X syndrome, ring chromosome, chromosome inversion, isochromosome formation, translocation, or abnormal gene products.

Optionally allele-specific oligonucleotide hybridization may be employed in multifunctional array 200 in biosensor platform 102 to assist in direct gene diagnosis of mutations. Systems-biology platform 104 may diagnose genetic disease or mutation, such as Mendelian disorders, autosomal dominant disorders, autosomal recessive disorders, X-linked disorders, Marfan syndrome, Ehlers-Danlos syndrome, familial hypercholesterolemia, lysosomal storage diseases, Tay-Sachs Disease, Gangliosidosis, Niemann-Pick disease, Gaucher Disease, glycogen storage diseases, Mucopolysaccharidoses, Alkaptonuria, Neurofibromatosis, trisomy 21, chromosome 22q11 deletion syndrome, Klinefelter syndrome, XYY syndrome, Turner Syndrome, Multi-X females, hermaphroditism, pseudohermaphroditism, triplet repeat mutations, chromosome-breakage syndrome, Prader-Willi syndrome, Angelman syndrome, or gonadal mosaicism.

Alternatively, systems-biology platform 104 may diagnose infectious disease or infection, such as Haemophilus influenzae infection, tuberculosis, histoplasmosis, coccidioidomycosis, shigella bacillary dysentery, Campylobacter enteritis, Yersinia enteritis, Salmonellosis, typhoid fever, cholera, amebiasis, giardiasis, herpes, chlamydia, gonorrhea, syphilis, trichomoniasis, staphylococcal infection, streptococcal infection, clostridial infection, measles, mumps, mononucleosis, polio, chickenpox, shingles, whooping cough, diptheria, infections associated with Neutropenia and Helper-T cell depletion, cytomegalic inclusion disease, pseudomonas infection, legionnaires disease, listeriosis, candidiasis, cryptococcosis, aspergillosis, mucormycosis, pneumocystis pneumonia, cryptosporidium and cyclospora infection, toxoplasmosis, dengue fever, Rickettsial Infection, trachoma, leprosy, plague, relapsing fever, lyme disease, malaria, babesiosis, leishmaniasis, African Trypanosomiasis, Chagas disease, Trichinellosis, hookworm, cysticercosis, Hydatid disease, schistosomiasis, lymphatic filariasis, or onchocerciasis.

In diagnosing infectious disease or infection, systems-biology platform 104 receives data from sensor unit 111 or neural networks, artificial intelligence, fuzzy systems, or probabilitic systems that consider presence of infectious agent, such as a prion, virus, bacteriophage, plasmid, transposon, chlamydiae, rickettsiae, mycoplasma, fungi, protozoa, helminths, or ectoparasite. In host system, systems-biology platform 104 may also consider the presence of bacterial endotoxin, bacterial exotoxins, proliferation and morphologic lesions of epithelial cells, tissue necrosis, granulomas, cysts, increased levels of leukocytes, mononuclear cells or neutrophils, mononuclear interstitial infiltrates, reduced levels of immune cells (e.g. cytokines, lymphocytes, macrophages, dendritic cells or natural killer cells), bacterial leukotoxins, hemagglutinin, spores, or other antigen or protein from bacteria, virus, fungi, protozoa, or parasite.

Alternatively systems-biology platform 104 may diagnose disease of immunity, such as hypersensitivity disorders (immune complex mediated, complement-dependent reactions, cell mediated, or anaphylactic type, transplant rejection), autoimmune disease, systemic sclerosis, inflammatory myopathies, mixed connective tissue disease, polyarteritis nodosa or other vasculitides, X-linked agammaglobulinemia of Bruton, common variable immunodeficiency, isolaged IgA deficiency, Hyper IgM syndrome, DiGeorge syndrome, severe combined immunodeficiency disease, immunodeficiency with thrombocytopenia and eczema, acquired immunodeficiency syndrome (AIDS), or amyloidosis.

In diagnosing immunity diseases, systems-biology platform 104 considers following sensed, detected, or measured conditions from sensor unit 111: levels of immune cells (e.g., mast cells, cytokines, lymphocytes, macrophages, dendritic cells or natural killer cells), MHC (major histocompatibility complex) molecules or antigens, HLA (human leukocyte antigen) complex, antigens, or types, or levels of primary mediators (e.g., biogenic amines, chemotactic mediators, enzymes, or proteoglycans), secondary mediators (e.g., leukotrienes, prostaglandins, platelet-activating factors, or cytokines), histamines, platelet-activating factor (PAF), neutral proteases, chemotactic factors, or antigen-presenting cells (APC).

In diagnosing autoimmunity diseases, systems-biology platform 104 receives data from sensor unit 111 or neural networks, artificial intelligence, fuzzy systems, or probabilistic systems considers presence of auto-antibodies disease and considers whether auto-antibodies are directed against single organ or cell type or whether it is systemic. Autoimmune diseases include single organ or cell type related diseases (e.g., hashimoto thryoiditis, autoimmune hemolytic anemia, autoimmune atrophic gastritis of pernicious anemia, autoimmune encephalomyelitis, autoimmune orchitis, goodpasture syndrome, autoimmune thromcytopenia, insulin-dependent diabetes mellitus, myasthenia gravis, Graves disease), or systemic autoimmune diseases (e.g., systemic lupus erythmatosus, rheumatoid arthritis, Sjögren syndrome, or Reiter syndrome).

Systems-biology platform 104 may identify whether disease condition may be single organ or cell type autoimmune diseases or primary biliary cirrhosis, chronic active hepatitis, ulcerative colitis, or membranous glomerulonephritis. The platform is also identifies whether disease condition may be systemic autoimmune disease or inflammatory myopathies, systemic sclerosis (scleroderma) or polyarteritis nodosa.

Furthermore systems-biology platform 104 may determine presence of pathologic autoimmunity by considering at least three requirements, such as presence of autoimmune reaction, clinical or experimental evidence that such reaction is not secondary to tissue damage but of primary pathogenetic significance, or absence of another well-defined cause of disease.

Alternatively systems-biology platform may be used in diagnosis of neoplasia. In diagnosing neoplasia, systems-biology platform 104 receives sensed, detected, or measured data from sensor unit 111 and neural networks, artificial intelligence, fuzzy systems, or probabilistic systems considers the following factors: DNA damage, failure of DNA repair, mutations in the genome of somatic cells, activation of growth-promoting oncogenes, alterations in the genes that regulate apoptosis, inactivation of cancer suppressor genes, expression of altered gene products and loss of regulatory gene products, oncoproteins, growth factors, growth factor receptors, proteins involved in signal transduction, nuclear regulatory proteins, cell cycle regulators, tumor antigens, or the levels of immune cells (e.g., mast cells, cytokines, lymphocytes, macrophages, dendritic cells or natural killer cells).

Systems-biology platform 104 may consider epidemiological factors in determining diagnosis for neoplasia. Epidemiological factors may include cancer incidence, geographic or environmental factors (DNA damaging agents—e.g. chemicals, radiation or viruses), or heredity (e.g., inherited cancer syndromes, familial cancers, autosomal recessive syndromes of defective DNA repair). Systems-biology platform 104 may consider tumor markers such as hormones (e.g. human chorionic gonadotropin, calcitonin, catecholamine and metabolites, or ectopic hormones), oncofetal antigens α-fetoprotein or carcinoembryonic antigen), isoenzymes (e.g., prostatic acid phosphatase, or neuron-specific enolase), immunoglobulins, prostate-specific antigens or mucins or other glycoproteins (e.g. CA-125, CA-19-9, or CA-15-3).

After systems-biology platform 104 makes diagnosis, platform may recommend treatments in combination or individually. Such recommendation may include diet changes, surgery, radiation therapy, chemotherapy, medications, antiangiogenesis therapy, or other cancer treatment. Systems-biology platform 104 may instruct therapeutic unit 113 to manufacture or dispense pharmaceuticals, biopharmaceuticals, or other therapeutic tools for the treatment of neoplasia.

Systems-biology platform 104 may employ sensor device and simulation method for analyzing dynamic hormone-secretion phenomena in dynamic biological systems, for example using sensor, artificial neural network, and dosing device; e.g., Sicel Technologies wireless or telemetric sensor platform for measuring parameters of relevance in vivo, such as radiation dose, tissue microenvironment or gene expression to increase treatment success. Implantable sensors may be provided 2 mm diameter, 15 mm length, for injection at margin of tumors using minimally invasive procedure.

Biosensor 100 may be applied to food technology, e.g., pasteurization or development or production of artisan foods. DNA sensor 201 may monitor, detect, or measure amount of bacteria or microflora used to ripen and develop flavors in foods, such as artisan cheese. Similarly peptide or protein sensor 203, lipid or fatty acid sensor 208, or small molecule sensor 217 may monitor bacterial or microflora production of fats, proteins, esters, or other biologically-active molecules.

Biosensor 100 may be applied to food manufacturing industry, e.g., quality control, food safety, or countering food borne illness caused by bioterrorism. Biosensor 100 may detect types of food contaminants, including bacteria or chemicals that cause human sickness, or counter bioterrorism acts threatening consumer food supply.

Biosensor 100 may be used by food manufacturer, crop cultivator, lab researcher, consumer, packer, distributor, receiver, food vendor, or food inspector to ensure quality control and food safety. Biosensor platform 102 may detect, measure, or determine presence or absence of parasitic organism, virus, bacteria, fungi, protozoa, or unicellular or multicellular organism present during food manufacturing process or growth of food crops, or prior to consumption.

Chemical sensor 216 may be used to sense, detect, or measure foreign chemicals, such as toxins, vitamins, minerals or other organic and inorganic chemicals. Systems-biology platform 104 may analyze raw data from biosensor platform 102 to identify potentially-hazardous organism or chemical or flag unknown organism or chemical.

When systems-biology platform 104 identifies or quantifies potentially hazardous organism or chemical or unknown organism or chemical, data is stored in storage 105. Systems-biology platform 104 may generate report document or electronic multi-media warning or signal, which discloses detected organism or chemical and determine whether manufacturing, crop growth, or consumption is safe to continue.

Systems-biology platform 104 may send automated warning or signal, sent via wireless communication 106, to information recipient interested in data gathered by the platform, such as remote database, researcher, lab, government agency, or health or safety maintenance organization.

Chemical sensor 216 may determine purity or verify amount of vitamin, mineral, herb, or botanical claimed by a food product, meal supplement, vitamin supplement, or other nutritional substance. Systems-biology platform 104 may compare amount of vitamin, mineral, herb or botanical determined by chemical sensor 216 to pre-set amount or range stored in storage 105, e.g. amount or range determined by government agency or health or safety maintenance organization.

Systems-biology platform 104 generates report whether detected amount or range complies with pre-set amount or range, and determines whether manufacturing or consumption is safe to continue. Detected amount can be reported and sent via wireless communication 106 to outside source or information recipient interested in data gathered by chemical sensor 216, such as packer, distributor, receiver, remote database, researcher, lab, government agency, or health or safety maintenance organization. During manufacturing, determined amount of vitamin, mineral, herb, or botanical present in each lot or batch of produced product is recorded or accessible through network 103 for analysis.

Optionally if amount of vitamin, mineral, herb, or botanical falls outside pre-set amount or range, systems-biology platform 104 generates automated warning to outside source or information recipient. Biosensor 100 monitors manufacturing of food product, meal supplement, vitamin supplement, or other nutritional substance by ensuring that manufactured substance complies with required amount or range of nutritional substance. Chemical sensor 216 may be used to demonstrate whether particular vitamin, mineral, herb, botanic, or other natural or organic food has properly absorbed in biological system of organism.

Biosensor 100 may synchronize different input stimuli, particularly with integrated purpose of evaluating food and drug interactions positively or negatively within host. Systems-biology platform 104 can analyze genetic composition of host, determined through DNA sensor 201, to assist in predicting particular drug-food interactions. To assist in predicting drug and food interactions, host genetic composition may be supplemented with additional information or test data including nongenetic (e.g. environmental, epidemiological) or immunological factors relating to host.

Biosensor 100 may be implanted within a host and pharmacogenetics 304 or pharmacokinetics 308 in systems-biology platform 104 may be employed to monitor or determine activity or effectiveness of medication used individually or in combination. Meanwhile, biosensor 100 placed remotely or separately from implanted biosensor is used to analyze nutritional substance (e.g., food product, meal supplement, vitamin, or mineral) that may be consumed by same host.

Data from remote biosensor 100 is coupled, received, or combined to data from implanted biosensor or analyzed collectively by systems-biology platform 104 to predict or model combined allergic reactions, side effects, or adverse reactions that result from consumption of nutritional substance in conjunction temporally with related medication.

Systems-biology platform 104 may generate automated recommendation or report diagnostically or therapeutically about optimum level of nutritional substance or identify alternative substance for consumption. Data from remote and implantable biosensor data, and recommendation or determination processed by systems-biology platform 104 may be stored in data storage 105. An outside source or information recipient may access data and results in data storage 105 through wireless communication 106 for analysis via network 103.

When systems-biology platform 104 identifies nutritional substance that may cause an adverse or positive reaction, automated warning or message may be transmitted wirelessly to information receipt interested in the gathered data. The ability of systems-biology platform to analyze or model nutritional substance and host condition in combination using host sensor data and consumable sensor data optimizes treatment of real-time physiological condition.

Biosensor 100 may be applied to biopharming purpose, e.g., field tests or inspections of genetically engineered plants, and use of genetically engineered plants or transgenic crops to produce therapeutic proteins and industrial enzymes with safeguards for ensuring that food crops are not co-mingled with food crops intended for pharmaceutical or industrial use.

To prevent out-crossing or commingling of genetic material, DNA sensor 201, RNA sensor 202, or peptide and proteins sensor 203 in biosensor platform 102 may detect, sense or measure presence or absence of foreign genetic material or protein in food crop not intended for pharmaceutical or industrial use. Systems-biology platform 104 may analyze raw data from biosensor platform 102 to identify out-crossing or commingling of genetic material.

When systems-biology platform 104 identifies foreign genetic material, data is stored in storage 105. Systems-biology platform 104 may generate report about detected foreign genetic material or determine whether crop growth is safe to continue. Systems-biology platform 104 may send automated warning or signal, via wireless communication 106, to information recipient interested in data gathered by platform, such as remote database, researcher, lab, government agency, or health or safety maintenance organization.

Biosensor 100 may monitor growth of food crops, e.g., sensors (e.g. peptide or protein sensor 203, vector or virus vector sensor 207, pH sensor 212, metabolites sensor 219, etc.) in biosensor platform sensor 201 may sense, detect or measure abnormalities in crop growth or reproduction. Biosensor 100 may monitor, detect or measure pesticides, insecticides or foreign chemicals effect on growth or reproduction.

Biosensor 100 may be applied to bio-manufacturing industry, e.g., drug-producing plants and transgenic animals, such as cows genetically transformed to excrete different kinds of therapeutic proteins in breast milk. Peptide or protein sensor 203 in biosensor platform 102 or antibody sensor 204 may detect or measure presence or absence of genetically engineered therapeutic protein or antibody in breast milk or other biological fluid.

Biosensor 100 may be applied in xenotransplantation, for example by screening animal organs for transplantation into humans. Sensor unit 111 senses, measures, or processes biological molecule, such as cell, tissue, or intracellular or extracellular material from animal cell, tissue or organ, or raw data is analyzed by system biology platform 104. System biology platform 104 analyzes or determines whether animal cell, tissue, or organ is compatible for use with human for transplantation or other therapeutic process.

Biosensor 100 may be applied to avian transgenics, particularly to proteins produced through poultry-based production systems. For example, biosensor platform 10 may detect whether successful transformation is occurring via avian embryonic germ cell, retroviral-mediated transformation, sperm-mediated transgenesis, avian embryonic stem cell, direct egg transfection, or other transformation process.

Biosensor 100 may be applied to drug-producing plants, e.g., tobacco, corn, or other non-food plants, for biomanufacturing. Peptide or protein sensor 203 may detect, sense or measure presence, absence, manufacture or biological activity of recombinant proteins manufactured in plants. DNA sensor 201, RNA sensor 202, vector or virus vector sensor 207, chromosome sensor 221, or cell sensor 222 may monitor or detect whether genetic material, vector, chromosome, or cell successfully integrates or genetically transforms plant or animal.

Figure 3C:
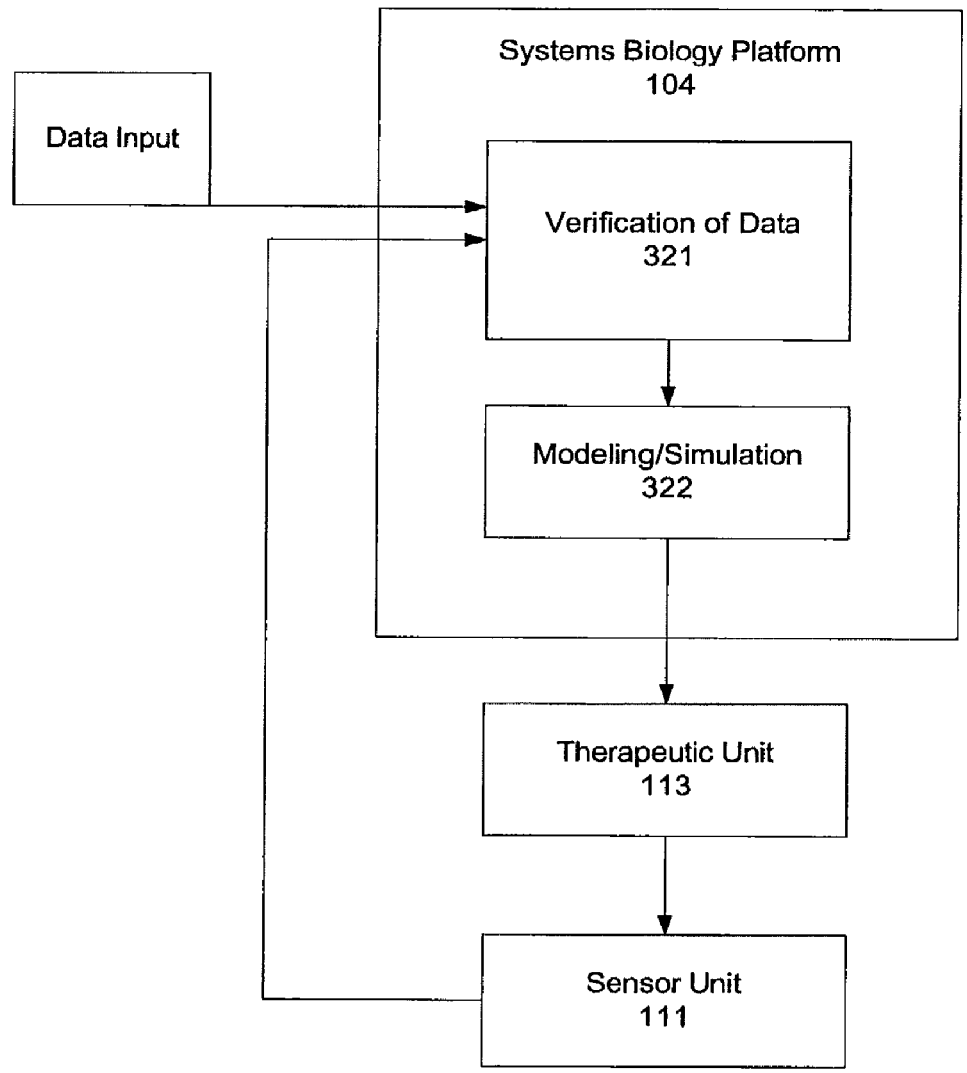
FIG. 3c shows system biology software and sensor according to aspect of present invention.

FIG. 3c systems-biology platform 104, therapeutic unit 113, and sensor unit 111. Systems-biology platform 104 provides verification of data 321, to assure that data is proper or feasible from biosensor platform 102 within sensor unit 111. Verification of data 321 identifies sequence or structures of target system. Data may be analyzed statistically by systems-biology platform 104, using statistical computation, e.g., scatter plot matrices, Venn diagrams, comparative histograms, volcano plots, or gene ontology charts. Computed statistics are interpreted biologically, filtering or reducing dataset to manageable size by eliminating results that show insignificant or uninteresting biological data.

Verification of data 321 includes checking regulatory relationship of genes or interaction of proteins that provide signal transduction or metabolism pathways, as well as physical structure of organisms, organelle, chromatin, cell-cell interactions, or other components.

To integrate sensor data, software and management systems are used. Systems-biology platform 104 may utilize management software, e.g., Analysis Information Management System (AIMS), using tools to analyze or manage range of complexity of data obtained from microarrays or assays, tracking computational processes. Data-mining tools, e.g., high-dimensional data analysis tools, may process data where data have multiple dimensions.

Data may be formatted using standardization programs, e.g., Gene Expression Markup Language (GEML), Microarray Markup Language (MAML), Microarray and Gene Expression Data (MAGE), MicroArray and Gene Expression Markup Language (MAGE-ML), solutions by by Microarray Gene Expression Database group (MGED) or Minimum Information About a Microarray Experiment (MAIME), or other programs.

After data is verified, modeling/simulation 322 uses combined simulation data or sensor signal to model biological structures or relative interactions. Modeling or simulation 322 simulates biological interactions to identify behavior of system, for example, sensitivity of behaviors against external perturbations and how quickly system returns to normal state after stimuli.

Another example includes simulating how individual malfunctioning mis-folded protein interacts with other proteins or cellular components, with simulations on how protein responds to particular therapies; yet another example is modeling phospho-proteomics and systems biological role for oncology target discovery or validation.

Modeling or simulation 322 predicts methods of controlling state of biological system, e.g., pharmaceutical or gene therapy transformation of malfunctioning cells into healthy cells. For example through structural analysis, regulation of c-Abl and STI-571 specificity may be achieved.

Modeling or simulation 322 prediction is translated into instructions for therapeutic unit 113 to implement appropriate therapy to fix biological system. These instructions are conveyed to therapeutic unit 113, where instructed therapy may be performed.

Sensing unit 111 monitors progress, efficiency, or ancillary effects of induced therapy on biological system. Data from sensing unit 111 may be verified by verification of data 321, which provides cyclical self-regulating process.

Figure 4A:
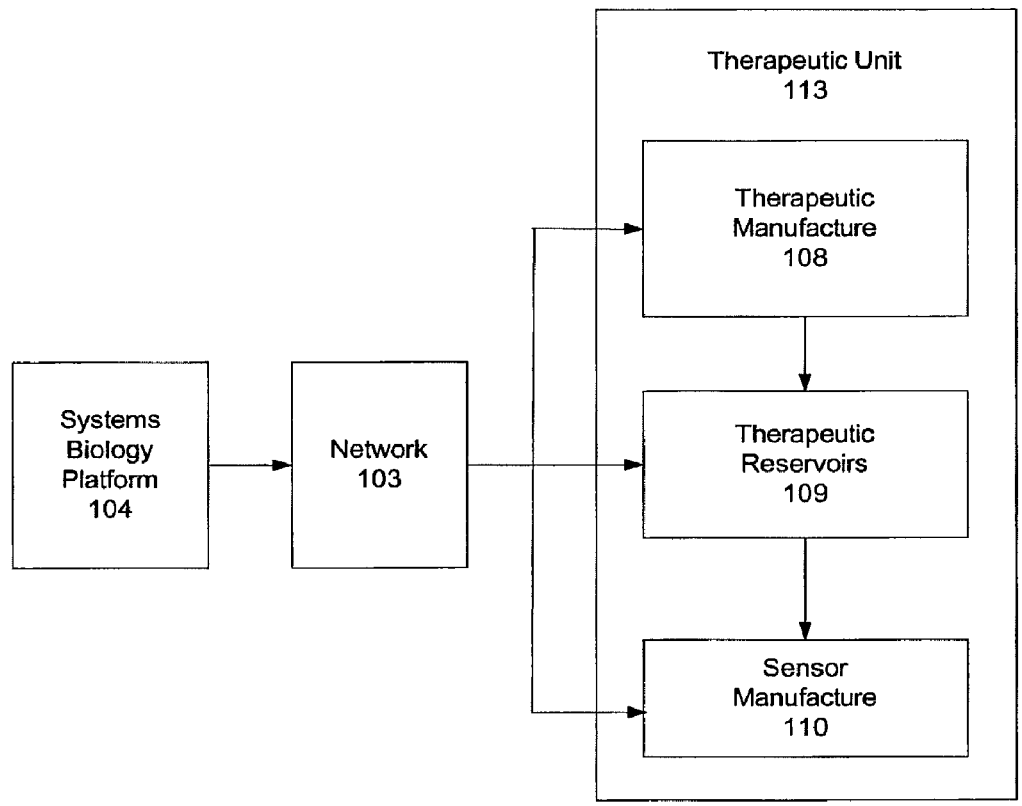
FIG. 4a shows system biology software according to aspect of present invention.

FIG. 4a shows flow of instructions from systems-biology platform 104 to network 103 to components comprising therapeutic unit 113. Components of therapeutic unit 113 include therapeutic manufacture 108, therapeutic reservoirs 109, and reconfigurable sensor manufacture 110. These components may be reconfigurable or software-programmable according to systems-biology platform 104, or from external source through wireless communication unit 106.

Figure 4B:
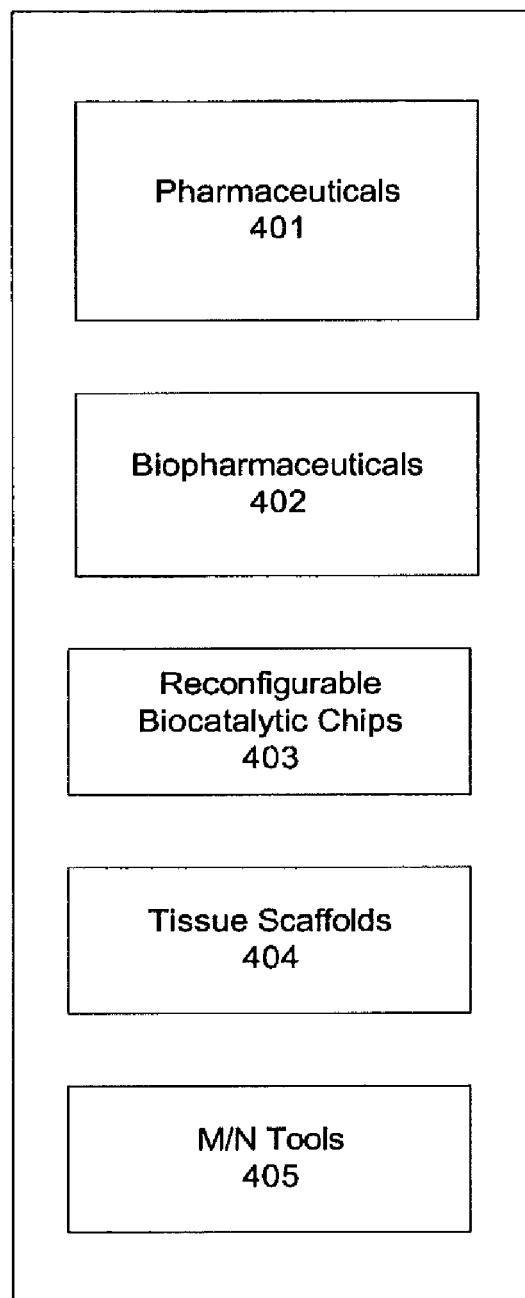
FIG. 4b shows therapy according to aspect of present invention.

FIG. 4b shows therapeutic manufacture 108 of: pharmaceuticals 401, biopharmaceuticals 402, tissue, reconfigurable biocatalytic chips 403, tissue scaffolds 404, M/N machines 405, or other therapeutic material or tools. These components may be reconfigurable and software-programmable according to systems-biology platform 104, or from external source through wireless communication unit 106.

Pharmaceuticals 401 may be known and matched with organism, or computationally derived or optimized from systems-biology platform 104. Pharmaceuticals 401 is defined herein as including chemical substance that provides benefit to system.

Biopharmaceuticals can be naturally-occurring biological molecule or structural derivative of biological molecule. For example, biopharmaceuticals can be isolated DNA molecules, recombinant DNA molecules, DNA fragments, oligonucleotides, antisense oligonucleotides, RNA molecules or constructs, self-modifying RNA molecules, catalytic RNAs, ribozymes, modified ribozymes, synthetic peptides, peptide linkers, proteins, fusion proteins, antibodies, modified antibodies, antigens, cell surface receptors, monoclonal antibodies specific for epitopes, polyclonal antibodies, tissue factors, modified tissue factors, mutant tissue factors, ligands, vectors, virus strains for gene transfer, recombinant plant viral nucleic acids, bacterial strains, oil-body proteins as carries of high-value peptides in plants, host cells, transformed cells, or microorganisms newly isolated in pure form from natural source.

Therapeutic unit 108 may prepare biopharmaceutical product such as 2 vg of sub50-nm tenascin nanocapsules containing antisense of protein kinase CK2 $\alpha$ subunit or similarly GFP and RFP-labeled bacteria which produce toxins or other therapeutic proteins to be used to target tumors. Further therapeutic unit 108 can perform functions like so-called Intelligent Pill (e.g., University of Calgary) in which information relayed to chip that controls micropumps that squeeze-out therapeutic material.

Therapeutic manufacture unit 108 may prepare therapy comprising pharmaceutical 401 or biopharmaceutical aspect 402. For example antiangiogenesis therapy using yttrium-90 nanoparticles with conjugated anti-Flk-1 monoclonal antibody administered by i.v. injection is anti-angiogenic agent for treatment of solid tumors. Therapeutic manufacture unit 108 may produce small interfering RNA (siRNA) used to inhibit P-gp encoded by MDR1 gene; production enhances accumulation of sensitivity of multidrug-resistant cancer cells to drugs transported by P-glycoprotein.

Reconfigurable biocatalytic chips 403 are software programmable from instructions by systems-biology platform 104, or from external source through wireless communication unit 106. Depending on instructions, reconfigurable biocatalytic chips 403 can be activated, deactivated, manufactured, or disassembled. Reconfigurable biocatalytic chips 403 undergo molecular bioprocessing, fabricating or manipulating single and multienzyme systems on biochip to induce artificially biocatalysis in system.

Tissue scaffolds 404 may be reconfigurable, and controlled by systems-biology platform 104 instructions (or from external source through wireless communication unit 106). Scaffold 404 may be substrate to grow cells or tissues, which may be activated or deactivated according to signaled instructions. Permanent or biodegradable tissue scaffolds can be used. Further scaffold 404 may be personalized by systems-biology platform, e.g., John Hopkins University stem cell-based polymer scaffolds for tissue engineering using composite hydrogel. After modeling tissue development on biomaterial scaffolds based on individualized systems-biology profile, reconfigurable scaffold 404 can be programmed with biological signals based on individual need.

M/N tools 405 may perform therapeutic treatments, e.g., Johnson & Johnson Cordis Corporation, that make drug coated stents that keep arteries from clogging by releasing medication. Examples of M/N tools may be self-assembling, e.g., Angstrom Medica altered calcium and phosphate molecules that self-assemble to create nanostructred synthetic bone.

Another tool example is S. Stupp project at Northwestern University, which provides long complex molecules with hydrophobic tails and hydrophilic heads; these molecules self-assemble to form cylindrical structures that can be applied to making artificial bone. Another example of M/N tools 405 is Son Binh Nguyen use of nanoparticles for small molecule chemotherapy, in which engineered hydrophobic cyclic peptides attaches to targeted molecules and subsequently chemically react with molecule, breaking it into pieces.

Figure 4C:
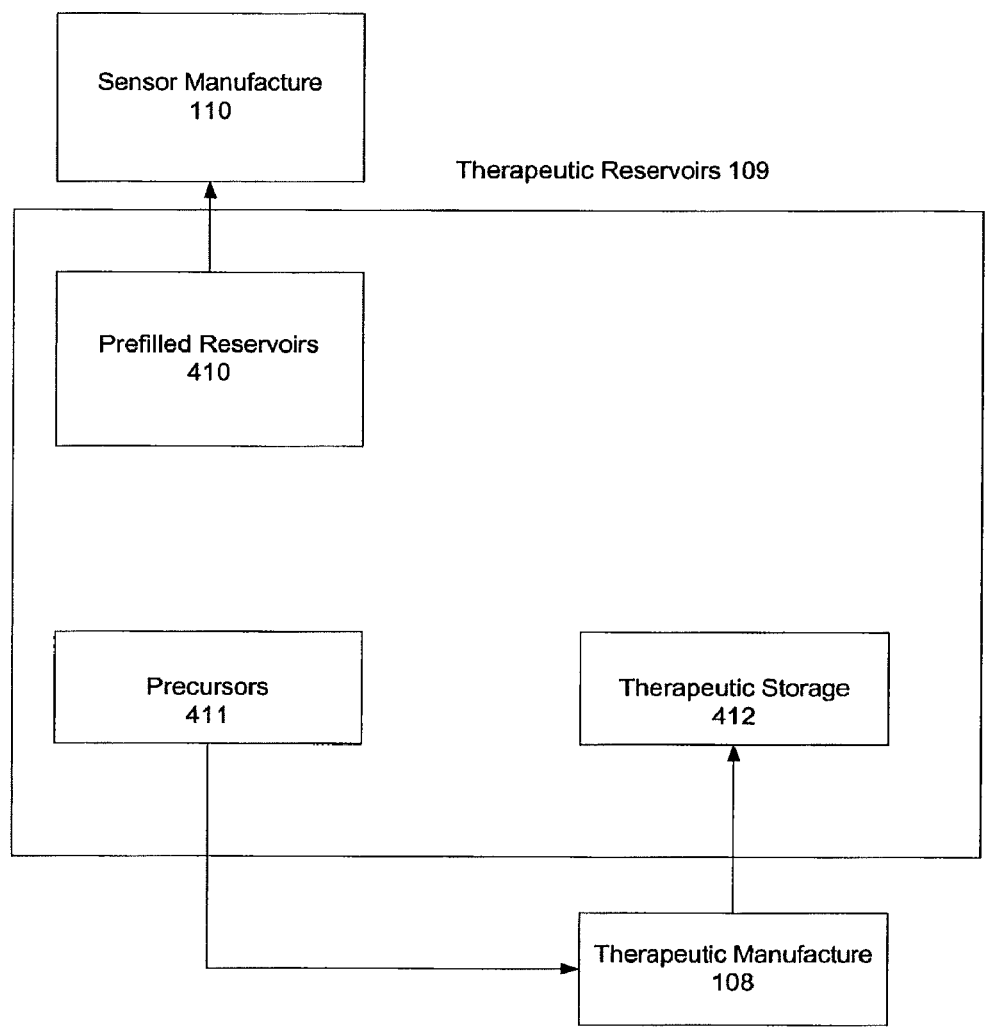
FIG. 4c shows therapy reservoir according to aspect of present invention.

FIG. 4c shows components of therapeutic reservoirs 109. Release of therapies is dictated or controlled by systems-biology platform 104 instructions, or from external source through wireless communication unit 106; timing mechanisms or rate of release may be reconfigured by software, e.g., MicroCHIPS implantable bioMEMS for drug delivery, in which silicon reservoirs hold medications in solid, liquid, or gel form, or iMEDD "NanoPORE Membranes," silicon wafers that have channels or pores with dimensions on nanometer scale for drug release.

Pre-filled reservoirs 410 contain medication filled-in biosensor 100 before implantation in living system. Contents of pre-filled reservoirs 410 may be pharmaceuticals or biopharmaceuticals in active form for release directly to living system. Pre-filled reservoirs 410 may hold probes, amino acids, nucleotides, or building blocks for sensor manufacture 110 for making additional biosensors.

Precursors 411 may be biological and chemical precursors to therapeutic pharmaceuticals and biopharmaceuticals. Depending on instructions from systems-biology platform 104, therapeutic precursors may be released, or therapeutic manufacture 108 may process into active pharmaceuticals or biopharmaceuticals.

Therapeutic storage 412 may store excess medication produced by therapeutic manufacture 108. Application of storing medication rather than manufacturing as needed if large doses, i.e., that cannot be made fast enough by therapeutic manufacture 108, are needed at time intervals.

Figure 4D:
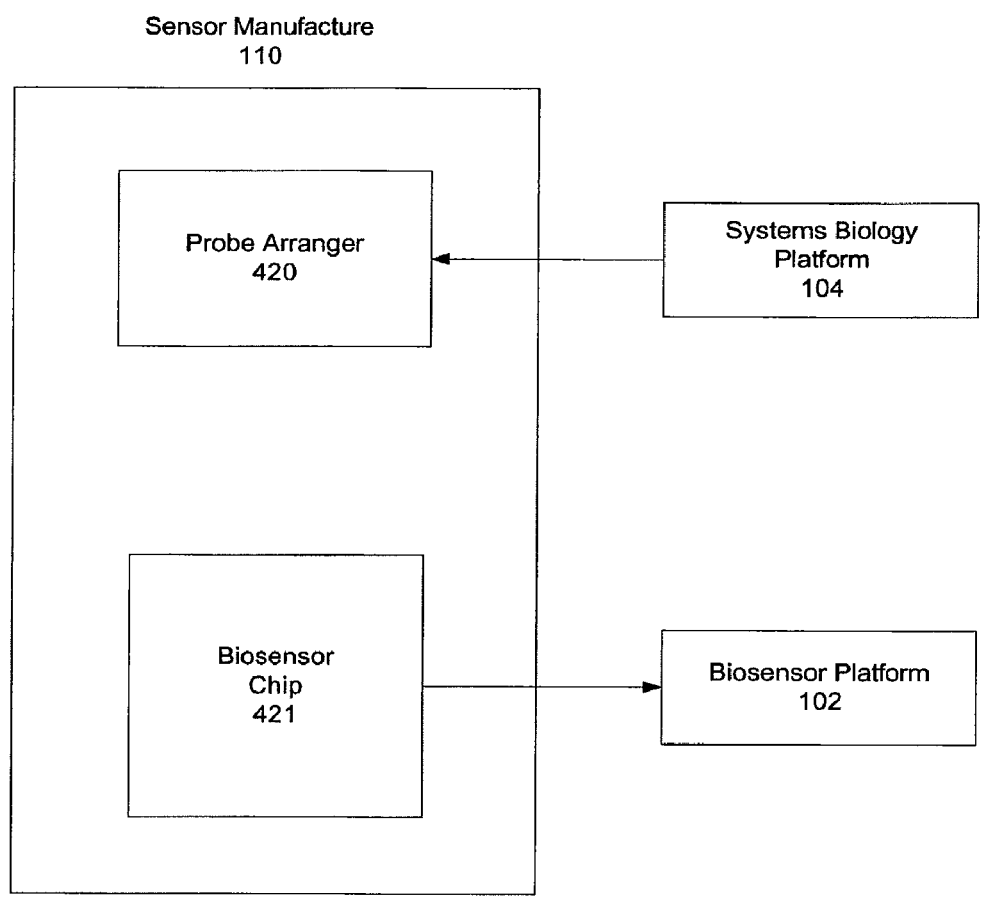
FIG. 4d shows sensor reconfiguration according to aspect of present invention.

FIG. 4d shows basic components or interactions of sensor manufacture 110. Systems-biology platform 104 sends software instructions to sensor manufacture 110 to dictate manufacture, disassembly, activation, or deactivation of software-programmable biosensors. Once reconfigurable biosensors are programmed and produced, such components and sensor data signals are integrated, multiplexed, or processed in combination into biosensor platform 102 for biological sensing.

Biosensor chip 421 acts as array or probe arranger 420 attaches probes onto array. Probe arranger 420 may attach probe for assaying, according to instructions by systems-biology platform 104. Method of attaching by probe arranger 420 can be printing method (e.g., placing probes on array with automated machinery). Probes may be attached through microspotting, in which automated microarray is produced by printing small quantities of pre-made biochemical substances onto solid surfaces.

Printing method may be ink-jet printing, e.g., GeSiM; non-contact method places probes on array, in which probes are sprayed on surface using piezoelectric or other propulsion to transfer biochemical substances from nozzles to solid surfaces, or directly placed. This method allows in situ synthesis, advantageously synthesizing oligonucleotides on-the-fly directly on array surface. To change DNA that may be placed on array, systems-biology platform 104 provides probe arranger 420 list of sequences to synthesize.

Another example of probe arranger 420 is photolithography, e.g., Affymetrix GeneChips. Photolithography allows oligonucleotides to be built base-by-base (e.g., proteins build amino acid-by-amino acid) on array surface by repeated cycles of photodeprotection and nucleotide or amino acid addition. Like ink-jet printing, this process allows building of M/N arrays without preexisting probes and can generate probes in situ on surface of biosensor chip 421.

Customizable microarray platform, e.g., CombiMatrix, including semiconductor-based desktop microarray platform may fabricate custom oligonucleotide biochips. Microarrays with unique content are designed and fabricated on-the-fly using software driven process to generate reagents electrochemically. DNA oligonucleotides are synthesized in situ according to probe sequence designed. Probe arranger 420 may use cell-positioning chip, e.g., Aviva chip, to provide living whole-cell arrays.

Optionally soft lithography may use stamp to pattern surfaces of array, using patterned elastomer based on program instructions to define microfluidic networks on surface.

Figure 5:
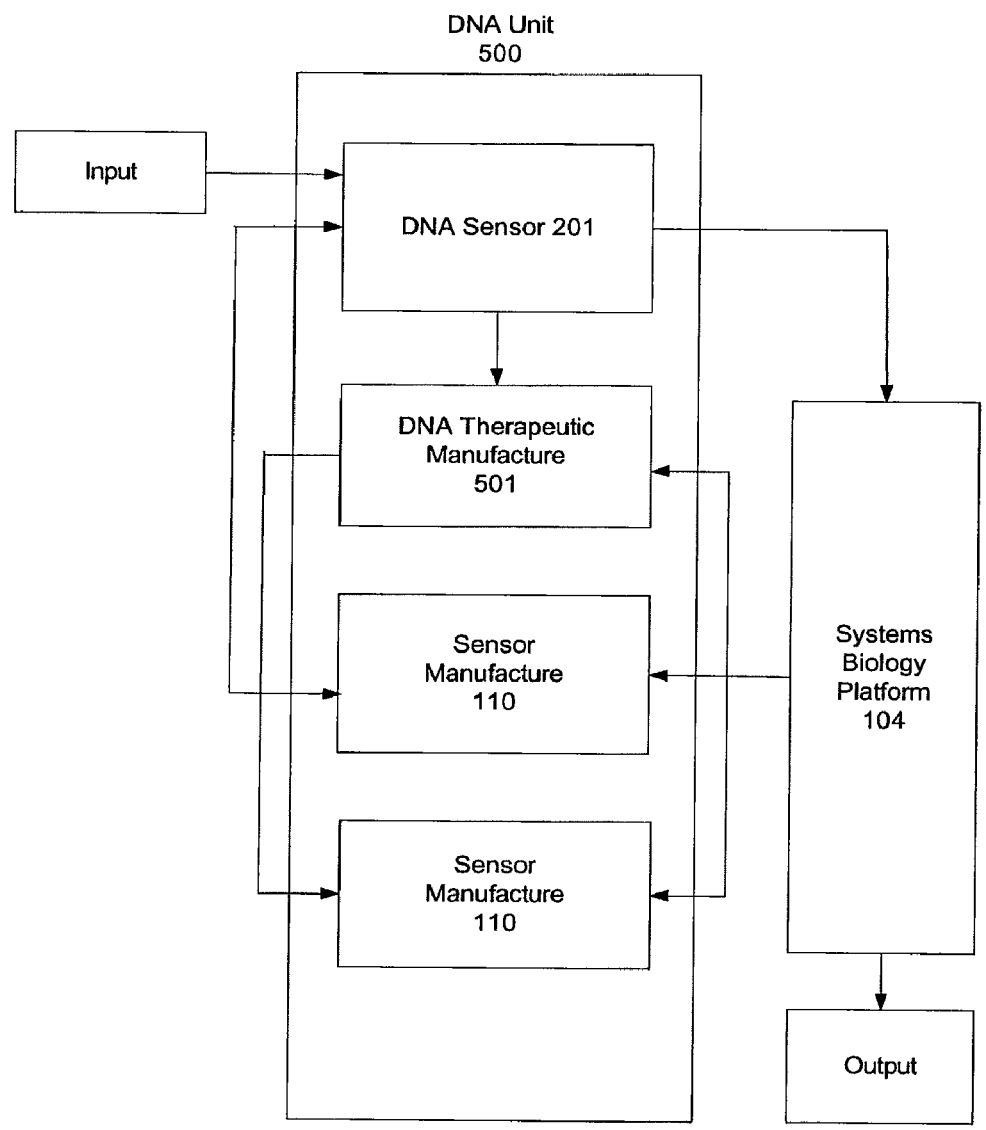
FIG. 5 shows DNA sensor according to aspect of present invention.

FIG. 5 shows DNA unit 500, representing organization of sensors in biosensor platform 102, such as RNA sensor 202, peptide or protein sensor 203, etc. DNA unit 500 may include DNA sensor 201, DNA therapeutic manufacture 501, DNA therapeutic reservoirs 502, or DNA reconfigurable biosensor 503 together in same physical structure, which lay in close proximity with each other. DNA therapeutic manufacture 501 is structure-specific category of therapeutic manufacture 108. DNA therapeutic reservoirs 502 and DNA reconfigurable biosensor 503 are structure-specific categories of therapeutic reservoirs 109 and sensor manufacture 110 respectively.

Sequential steps begin with input introduction into DNA unit 500, specifically DNA sensor 201. Raw data is transferred to systems-biology platform 104, a remote source. Systems-biology platform 104 processes information, outputting data and giving instructions to DNA therapeutic manufacture 501, DNA therapeutic reservoirs 502, and DNA reconfigurable biosensor 503. DNA therapeutic manufacture 501, DNA therapeutic reservoirs 502, and DNA reconfigurable biosensor 503 perform instructed tasks, with DNA sensor 201 monitoring respective progress.

DNA sensor 201 monitors or senses organism response to therapies dispensed by DNA therapeutic manufacture 501, DNA therapeutic reservoirs 502, or DNA reconfigurable biosensor 503. Proximity of DNA sensor 201, DNA therapeutic manufacture 501, DNA therapeutic reservoirs 502, or DNA reconfigurable biosensor 503 within same unit facilitates monitoring from DNA sensor 201.

Ongoing feedback is transmitted from DNA sensor 201 to DNA therapeutic manufacture 501, DNA therapeutic reservoirs 502, and DNA reconfigurable biosensor 503, while responding continually to DNA sensor 201 raw data, creating cyclic system of monitoring or responding.

Figure 6:
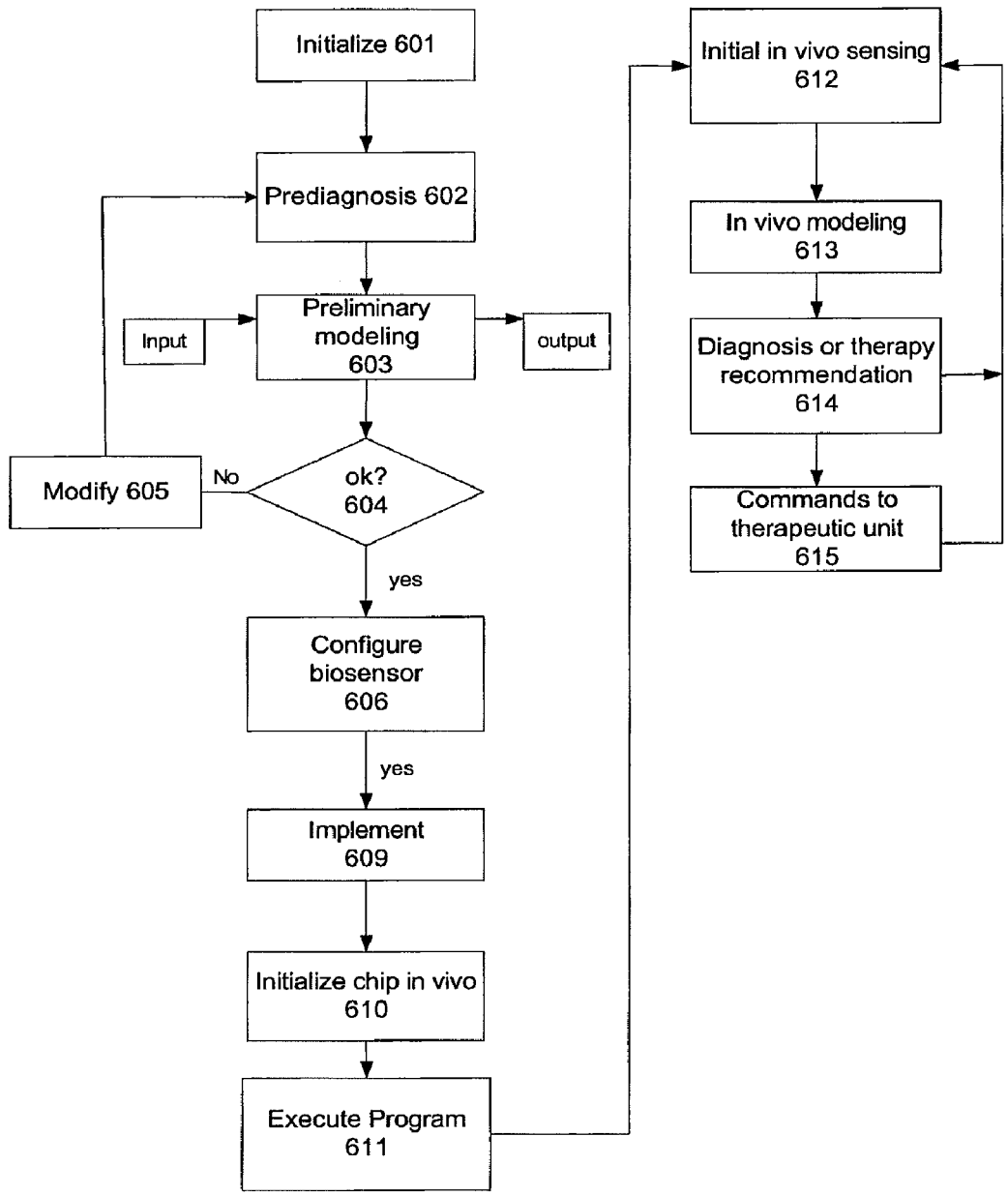
FIG. 6 shows diagnosis or therapy method according to aspect of present invention.

FIG. 6 flow chart shows automated or computer-assisted diagnosis or therapy recommendations or reports for target host, which is identified initially for possible diagnosis or treatment 601. To determine if host benefits from diagnosis or treatment, host undergoes preliminary screening 602. Preliminary screening may be implemented through software form; host undergoes preliminary modeling 603.

Modeling or simulation is used to model appropriate components or characteristics of device. After preliminary modeling 603, behavior of model is verified for accuracy 604. If behavior of model is not ok, biosensor 100 is modified 605, and preliminary modeling 603 is repeated. If behavior of model is ok 604, biosensor 100 is configured 606. Reconfigurable biosensor is made or programmed according to such model.

Reconfigurable biosensor may be verified to comply or adhere to FDA regulations 607. If biosensor does not comply or adhere, it is modified 608 and configuration 606 or verification of adherence to FDA regulations 607 is repeated. If biosensor does comply or adhere to FDA regulations, it is implanted or attached to host. 609.

Biosensor is initialized to allow sensor or detection activity in vivo 610. Sensing or software is executed 611. Initialization of biosensor and execution of sensing or software may operate in sequential order or in parallel. Once biosensor and software is initialized, initial in vivo sensing begins 612. Sensor data is then used for in vivo modeling 613 via systems-biology platform 104. After in vivo modeling 613, biosensor 100 generates diagnosis or therapy recommendation 614.

Therapy recommendations may result in commands to therapeutic unit 615 for therapeutic manufacturing or dispensing. Ongoing feedback between initial in vivo sensing 612, diagnosis or therapy recommendations 614, or commands to therapeutic unit creates an automated sensing, modeling, and treatment cycle.

Foregoing descriptions of specific embodiments of the invention have been presented for purposes of illustration and description. They are not intended to be exhaustive or to limit the invention to precise forms disclosed. Modifications and variations are possible in light of above teaching.

Embodiments were chosen or described in order to explain principles and application of the invention, thereby enabling others skilled in the art to utilize the invention in various embodiments or modifications according to particular purpose contemplated. Scope of the invention is intended to be defined by claims appended hereto and equivalents.

The invention claimed is:

1. Implantable network bio sensor comprising:
 a sensor unit having a positioning chip and a bio sensor platform, wherein the sensor unit senses a biological material using the positioning chip to position the biological material via micro-fluidic multi-channels, such that the sensor unit monitors biological material electrophysiology implantably using the biosensor platform to generate a sensor signal according to multi-functional bio sensing of the biological material;
 a controller having a network, a systems biology platform, a data storage, and a wireless communication, wherein the controller accesses wirelessly a data storage coupled to the network via the wireless communication to process the systems biology platform stored in the data storage remotely by simulating a systems biology model of the sensed biological material using the sensor signal to generate a simulation data; and
 a therapeutic unit having a therapeutic manufacture, therapeutic reservoir, and a sensor manufacture, wherein the therapeutic unit dispenses in-vivo therapeutic pharmaceutical or biopharmaceutical or precursors thereof using a biocatalytic chip that activates the therapeutic manufacture or therapeutic reservoir to dispense the pharmaceutical, biopharmaceutical or precursors thereof automatically according to a therapy instruction conveyed by the systems biology platform when processing a combination of the sensor signal and the simulation data to generate the therapy instruction, whereby the systems biology platform recalculates the therapy instruction to reconfigure the therapeutic unit adaptively in response to supplemental sensing by the sensor manufacture according to newly sensed interaction to the dispensed therapeutic pharmaceutical, biopharmaceutical or precursor thereof.

2. Implantable network bio sensor of claim 1 wherein:
 the sensor unit is reconfigurable adaptively by a simulator using a systems biology model.

* * * * *